US007767407B2

(12) United States Patent
Baranov et al.

(10) Patent No.: US 7,767,407 B2
(45) Date of Patent: *Aug. 3, 2010

(54) ELEMENTAL ANALYSIS OF TAGGED BIOLOGICALLY ACTIVE MATERIALS

(75) Inventors: Vladimir Baranov, Richmond Hill (CA); Scott Tanner, Aurora (CA); Dmitry Bandura, Aurora (CA); Zoe Quinn, Toronto (CA)

(73) Assignee: PerkinElmer Health Sciences, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/932,213

(22) Filed: Oct. 31, 2007

(65) Prior Publication Data

US 2008/0176334 A1 Jul. 24, 2008

Related U.S. Application Data

(60) Division of application No. 10/614,115, filed on Jul. 3, 2003, which is a continuation-in-part of application No. 09/905,907, filed on Jul. 17, 2001, now Pat. No. 7,135,296.

(60) Provisional application No. 60/258,387, filed on Dec. 28, 2000.

(51) Int. Cl.
*G01N 33/53* (2006.01)
(52) U.S. Cl. ...................... 435/7.1; 435/7.21; 435/7.92; 435/7.93; 436/501; 436/518; 424/1.41; 424/85.1
(58) Field of Classification Search ....................... None
See application file for complete search history.

(56) References Cited

U.S. PATENT DOCUMENTS

| | | | | |
|---|---|---|---|---|
| 4,022,876 A | * | 5/1977 | Anbar | 436/542 |
| 4,205,952 A | * | 6/1980 | Cais | 436/518 |
| 4,313,734 A | | 2/1982 | Leuvering | |
| 4,411,993 A | | 10/1983 | Gillis | |
| 4,444,879 A | | 4/1984 | Foster et al. | |
| 4,454,233 A | | 6/1984 | Wang | |
| 4,543,439 A | | 9/1985 | Frackelton, Jr. et al. | |
| 4,637,988 A | | 1/1987 | Hinshaw et al. | |
| 4,902,614 A | | 2/1990 | Wakabayashi et al. | |
| 5,071,775 A | * | 12/1991 | Snapka et al. | 436/545 |
| 5,521,289 A | * | 5/1996 | Hainfeld et al. | 530/391.5 |
| 5,907,034 A | | 5/1999 | Bosslet et al. | |
| 5,958,783 A | | 9/1999 | Josel et al. | |
| 6,140,638 A | | 10/2000 | Tanner et al. | |
| 6,242,735 B1 | * | 6/2001 | Li et al. | 250/288 |
| 6,428,956 B1 | * | 8/2002 | Crooke et al. | 435/6 |
| 6,746,679 B2 | | 6/2004 | Nathoo | |
| 6,770,266 B2 | | 8/2004 | Santarpia, III et al. | |
| 7,135,296 B2 | * | 11/2006 | Baranov et al. | 435/7.1 |
| 2002/0136929 A1 | | 9/2002 | Oikawa et al. | |
| 2003/0089886 A1 | | 5/2003 | Montgomery | |

FOREIGN PATENT DOCUMENTS

| | | | |
|---|---|---|---|
| WO | 9945150 | | 9/1999 |
| WO | WO 99/45150 | * | 9/1999 |
| WO | 0036136 | | 6/2000 |
| WO | 02054075 | | 7/2002 |

OTHER PUBLICATIONS

Nielsen et al. (Spectrochimica Acta Part B, 53, 1998, 339-345).*
Burgstaller et al. (Current Opinion in Drug Discovery and Development, 2002, vol. 5, No. 5, pp. 690-700—Abstract Only).*
Alredo Sanz-Medel et al., "Trace element specification by ICP-MS in large biomolecules and its potential for proteomics", Anal. Bioanal Cham (2003) 377:236-247.
Andrew Taylor et al., "Atomic spectrometry update. Clinical and biological materials, foods and beverages", J. Anal. At. Spectrom., 2003, 18, pp. 385-427.
An-Ping Deng et al., "Reaction cell inductively coupled plasma mass spectromety-based immunoassay using ferrocene tethered hydroxysuccinimide ester as label for the determination of 24-dichlorophenoxyacetic acid", Analytical Chimica Acta, 472, 2002, pp. 55-61.
Baldwin, G.S. et al., "Biologically active rexombinant human prograstrin6-80 contains a tightly bound calcium ion", J. Biol. Chem. 276: 7791-7796, 2001.
Bandura D. R., et al., "Effect of collisional damping and reactions in a dynamic reaction cell on the precision of the isotope ratio measurements" J. Anal. At. Spectrom., 15: 921-928, 2000.
Baranov., V.I. et al., "A sensitive and quantitative element-tagged immunoassay with ICPMS detection", Analytical Chemistry, Apr. 2002, vol. 74 No. 7, 1, 1629-1636.
Baranov, V.I., "A Dynamic Reaction cell for Inductively Coupled Plasma Mass Spectrometry (ICP-DRC-MS). Part 1. The rf-field energy contribution in thermodynamics of ion molecule reactions" J. Anal. At. Spectrom. 14: 1133-1142, 1999.

(Continued)

*Primary Examiner*—Lisa V Cook
(74) *Attorney, Agent, or Firm*—Torys LLP

(57) ABSTRACT

Methods for the detection and measurement of tagged (labeled) biologically active materials in a sample are described. The tagged biologically active materials are detected using an atomic mass or optical spectrometer having a source of atoms or atomic ions. Element-labeled biologically active materials, comprising antibodies, antibody Fab' fragments, antigens, aptamers, protein complexes, growth factors, hormones, receptors and other biologically active materials attached to a stable elemental tag, can be used in specific binding assays and measured by elemental spectroscopic detection. Also described are methods for the determination of metals in samples of interest using specific antibodies to isolate the target metals and elemental spectroscopy for detection and quantitation. Kits are provided comprising reagents to detect and measure labeled biologically active materials or labeled competition analytes.

25 Claims, 11 Drawing Sheets

OTHER PUBLICATIONS

Bartel et al., "Isolation of new ribozymes from a large pool of random sequences" Science 261: 1411-1418 (1993).

Binet M.R.B. et al., "Detection of zinc/cadmium binding proteins in *E. coli* by gel electrophoresis-laser ablation inductively coupled plasma-mass spectrometry", Society for Experimental Biology Annual Meeting Apr. 2-6, 2001 C1. 158 Canterbury, UK.

Blake, D.A. et al., "Immunoassays for metal ions" Analytica Chimica Acta 37613-19, 1998.

Bordes, A.L. et al., "Simultaneous detection of three drugs labeled by cationic metal complexes at a naflon-loaded carbon paste electrode" Talanta 48: 201-208, 1999.

C. Zhang et al., "Application of Biological Conjugate between Antibody and Colloid Au Nanoparticles as Analyte to Inductively Coupled Plasma Mass Spectrometry", Analytical Chemistry, pp. 3-8, A-d, 2001.

Chao Zhang et al., "ICP-MS-based competitive immunoassay for the determination of total thyroxin in human serum" J. Anal. At. Spectrom., 2002, 17, pp. 1304-1307.

Chen, X et al., "Site-specific mass tagging with stable isotopes in proteins for accurate and efficient protein identification" Anal. Chem. 72: 1134-1143, 2000.

Csaki, A. et al., "Gold nanoparticles as novel label for DNA diagnostics", Expert Review of Molecular Diagnostics. Mar. 2002, vol. 2, No. 2, p. 89-94.

Darwish, I. A. et al., "One-step competitive immunoassay for cadmium ions: development and validation for environmental water samples", Analytical Chemistry 73: 1889-1895, 2001.

de Llano et al., "Electrothermal atomic absorption spectrometric diagnosis of familial hypercholesterolemia", Anal. Chem. 72, 2406-2413, 2000.

de Llano, J. et al., "Use of Inductively Coupled Plasma-Mass Spectrometry for the quantitation of the Binding and Uptake of Colloidal Gold-Low Density Lipoprotein Conjugates by Cultured Cells", Analytical Biochem. 243: 210-217, 1996.

Earl Freidman et al., "Methods for Labeling Thyroxine with Radioactive Iodine", Science, Apr. 2, 1948, Bol. 107, pp. 353-354.

Ellington et al., "In vitro selection of RNA molecules that bind specific ligands", Natue 346 (6287): 818-822 (1992).

Ellington et al., "Selection in vitro of single-stranded DNA molecules that fold into specific ligand-binding structures" Nature 355(6363); 850-852 (1992).

Evans et al., "A method for Characterization of Humic and Fulvic Acids by Gel Electrophoresis Laser Ablation Inductively Coupled Plasma Mass Spectrometry", They Royal Society of Chemistry, 2000, vol. 15, No. 2, Feb. 2000, pp. 157-161.

F.A. Cotton et al., 1972, Advanced Inorganic Chemistry: A Comprehensive Text, "Introduction to the transition Elements" Interscience Publishers, Advanced Inorganic Chemistry pp. 528-554.

Feng-Bo Wu et al., "Sensitive time-resolved fluoroimmunoassay for simultaneous detection of serum thyroid stimulating hormone and total thyroxin with Eu and Sm as labels", Analytical Biochemistry, 314 (2003), 87-96.

Qiu, J. et al., "A rapid polarographic immunoassay based on the anodic current of metal lebeling", Anal. Biochem. 240:13-16, 1996.

Gold, Larry et al., (1995) "Diversity of Oligonucleotide functions" Annual Review of Biochemistry vol. 64, p. 763-97.

Green L.S. et al., "Aptamers as reagents for high-throughput screening", Biotechniques, Eaton Publishing, Natick US, vol. 30, No. 5, May 2001, p. 1094-1095.

Hess, A. et al., "Transition metal labels on peptide nucleic acid (PNA) monomers", Chemical Communications, May 1999, United Kingdom, vol. 5, No. 10, May 1999, p. 8886.

Holmberg. R.C. et al., "Isolation of DNA aptamers that bind Ru(bby)2phen2=", Abstracts of Papers American Chemical Society, vol. 224, No. 1-2, 2002, p. INOR105 XP002325844.

International Search Report for PCT/CA01/01815, dated Apr. 24, 2002.

International Search Report for PCT/CA2004/000974.

J. Sabine Becker et al., "Determination of phosphorous and metals in human brain proteins after isolation by gel electrophoresis by laser ablation inductively coupled plasma source mass spectrmetry" J. Anal. At. Spectrom., 2004, 19: 145-152.

J. Sabine Becker et al., "Determination of phosphorus in small amounts of pretein samples by ICP-MS" Anal. Bioanal. Chem., 2003, 275: 561-566.

J. Sabine Becker et al., "Structural identification and quantification of protein phosphorylations alter gel electrophoretic separation using Fourier transformation cydotron resonance mass spectrometry and laser ablation inductively coupled plasma mass spectrometry", International Journal of Mass Spectrometry, 228 (2003) 985-997.

Joanna, Szpunar "Advances in analytical methodology for bioinorganic speciation analysis: metallomics metalloproteomics and heteroatom-tagged proteomics and metabolomics", Analyst, 2005, 130, 442-465.

John Marshall et al., "Atomic Spectrometry Update—Atomic Emission Spectrometry", Journal of Analytical Atomic Spectrometry, Jun. 1997, vol. 12, pp. 263R-290R.

Kohler, G. et al., "Continuous cultures of fused cells secreting antibody of predefined specificity", Nature 256: 495-497, 1975.

Korth, C. et al., "Prion (PrPSc)-specific epitope defined by a monoclonal antibody", Nature, 390 (6655), 74-77, 1997.

Laffling, A.J. et al., "A monoclonal antibody that enables specific immunohistological detection of prion protein in bovine spongiform encephalopathy cases", Neurosci. Lett. 300(2), 99-102, 2001.

Lorsch, et al., "In virto selection of RNA aptamers specific for cyanocobalamin", Biochem., 33(4): 973-982 (1994).

Maggio, Immunoenzyme technique I, CRC press a a980, pp. 186-187.

Paul K. Horan et al., "Quantitative Single Cell Analysis and Sorting", Science vol. 198, Oct. 14, 1977, pp. 149-157.

Mathias Wind et al., "Element and molecular mass spectrometry—an emerging analytical dream team in the life sciences", J. Anal. At. Spectrom., 2004, 19, 20-25.

Mire-Sluis et al., Journal of Immunological Methods, 186, 1995, pp. 157-160.

Nagaoka, M. et al., "Binding patterns of co-existing aluminium and iron to human serum transferrin studied by HPLC-high resolution ICP-MS", Analyst 135: 1962-1965, 2000.

Neilson et al., Laser ablation inductively coupled plasma-mass spectrometry in combination with get electrophoresis: a new strategy for speciation of metal binding serum proteins, Spectrochimica Acta Part B 53, Elsever Science B.V., 1995, 339-345.

Norbert Jakubowski et al., "Metallobiomolecules. The basis of life, the challenge of atomic spectroscopy", J. Anal. At. Spectrom., 2004, 19, 1-4.

P.A. Bartlett et al., "Synthesis of Water-Soluble Undecagold Cluster Compounds", J. Am. Chem. Soc. 100: 5085-5089. 1978.

Zoe A. Quinn et al., "Simultaneous determination of proteins using an element-tagged immunoassay coupled with ICP-MS detection", JAAS, 2002, 17, 892-896.

Zhang et al., "A Novel Combination of Immunoreaction and ICP-MS as a Hyphenated Technique for the Determination of Thyroid-Stimulating Hormone (TSH) in Human Serum", J. Anal. At. Spectrom. vol. 16, No. 12, Dec. 2001, pp. 1393-1396.

Ralf Krugger et al., "Characterization of a gadolinium-tagged modular contrast agent by element and molecular mass spectrometry", J. Anal. At. Spectrom., 2004, 19, pp. 852-857.

Renli MA et al., "Speciation of protein-bound trace elements by gel eletrophoresis and atomic spectrometry", Electrophoresis 2004, 25, 2469-2477.

Robert S. Houk et al., "Inductively Coupled Argon Plasma as an Ion Source for Mass Spectrometric Determination of Trace Elements", Anal. Chem. 1980, 52, 2283-2289.

Robertson et al., "Selection in vitro of an RNA enzyme that specifically cleaves single-stranded DNA" Nature 344 (6265): 467-468 (1990).

Schramel, P. (Canas '95, Colloquim Analytische Atomspedtroskopie, Konstanz, Germany, Apr. 2-7, 1995 (1996), Meeting Date 1995, 671-681, Abstract Only).

Segond von Banchet et al., "Non-radioactive localization of substance P binding sites in rat brain and spinal cord using peptides labelled with 1.4 nm gold particles", J. Histochem. Cytochem. 43: 821-827, 1995.

Sichun Zhang et al., "Simutaneous Determination of α-Fetoprotein and Free β-Human Chronic Gonadotropin by Element-Tagged Immunoassay with Detection by Inductively Coupled Plasma Mass Spectrometry", Clinical Chemistry, 50:7 (2004), 1241-1221.

Tanner, S.D. et al., "A dynamic reaction cell for inductively coupled plasma mass spectrometry (ICP-DRC-MS). Part II. Reduction of interferences produced within the cell", JASMS, 10: 1083-1094, 1999.

Tanner, S.S. et al., "A dynamic reaction cell for inductively coupled plasma mass spectrometry (ICP-DRC-MS). Part III. Optimization and analytical performance", J. Anal. At. Spectrom., 15: 1261-1269, 2000.

Turek et al., "Systematic evolution of ligands by exponential enrichment: RNA ligands to bacteriophage T4 DNA polymerase" Science 249(4968): 505-510 (1990).

V.I. Baranov et al., "ICP-MS as an Elemental Detector in Immunoassays, Speciation Without Chromatography", European Winter Conference on Plasma Spectrochemistry, Hafjell, Norway, Winter 2001, Book of Abstracts, pp. 85.

Vladimir I. Baranov et al., "A Sensitive and Quantitative Element-Tagged Immunoassay with ICPMS Detections", Anal. Chem. 2002, 74, 1629-1636.

Vladimir I. Baranov et al., "The potential for element analysis in biotechnology", J. Anal. At. Spectrom. 2002, 17, 1148-1152.

Wagenknecht, T. et al., "Localization of calmodulin binding sites on the ryanodine receptor from skeletal muscle by electron microscopy", Biophys. J. 67: 2286-2295, 1994.

Wenzel, T. et al., "Conformational constraints in protein degradation by the 20S proteasome", Nature structural Biol. 2:199-204, 1995.

Wind, M. et al., "Analysis of protein phosphorylation by capillary liquid chromatography coupled to element mass spectrometry with 31P detection and to electrospray mass spectrometry", Anal. Chem. 73: 29-35, 2001.

Shan et al. (PNAS, Mar. 14, 2000, 2000, vol. 97, No. 6, pp. 2445-2449).

Examiner's Interview Summary dated Jun. 22, 2004 for U.S. Appl. No. 09/905,907.
Examiner's Interview Summary dated Jan. 27, 2005 for U.S. Appl. No. 09/905,907.
Examiner's Interview Summary dated Aug. 31, 2005 for U.S. Appl. No. 09/905,907.
Examiner's Interview Summary dated Apr. 3, 2006 for U.S. Appl. No. 09/905,907.
Examiners Amendment dated Apr. 3, 2006 for U.S. Appl. No. 09/905,907.
Non-final Office Action for U.S. Appl. No. 10/614,115 dated Mar. 18, 2009.
Final Office Action for U.S. Appl. No. 10/614,115 dated Aug. 6, 2008.
Non-final Office Action for U.S. Appl. No. 10/614,115 dated Jan. 11, 2008.
Final Office Action for U.S. Appl. No. 10/614,115 dated Jun. 5, 2007.
Non-final Office Action for U.S. Appl. No. 10/614,115 dated Oct. 20, 2006.
Non-final Office Action for U.S. Appl. No. 09/905,907 dated Jun. 1, 2005.
Final Office Action for U.S. Appl. No. 09/905,907 dated Oct. 4, 2004.
Non-final Office Action for U.S. Appl. No. 09/905,907 dated Feb. 27, 2004.
Final Office Action for U.S. Appl. No. 09/905,907 dated Aug. 12, 2003.
Non-final Office Action for U.S. Appl. No. 09/905,907 dated Jan. 15, 2003.
Advisory Action for U.S. Appl. No. 09/905,907 dated Nov. 4, 2003.
Restriction Requirement for U.S. Appl. No. 09/905,907 dated Aug. 19, 2002.
Restriction Requirement for U.S. Appl. No. 10/614,115 dated Jun. 29, 2006.
Advisory Action for U.S. Appl. No. 10/614,115 dated Jan. 5, 2009.

* cited by examiner

US 7,767,407 B2

ELEMENTAL ANALYSIS OF TAGGED BIOLOGICALLY ACTIVE MATERIALS

RELATED APPLICATIONS

This is a divisional application of U.S. patent application Ser. No. 10/614,115 filed Jul. 3, 2003, which is a continuation-in-part application of U.S. patent application Ser. No. 09/905,907 filed Jul. 17, 2001 now issued as U.S. Pat. No. 7,135,296, and claiming priority to U.S. Provisional Patent Application No. 60/258,387 filed Dec. 28, 2000.

FIELD OF THE INVENTION

The present invention relates to kits comprising reagents for the detection and measurement of element tagged biologically active materials and element tagged competition analytes. The present invention also relates to methods for the detection and measurement of element tagged biologically active materials and further relates to the detection and measurement of elements in a sample of interest. More particularly, the present invention is directed to detection and measurement of tagged immunoglobulins, aptamers, antigens or analytes using an atomic mass or optical spectrometer having a source of atoms or atomic ions.

BACKGROUND OF THE INVENTION

Various methods are in use for the detection and measurement of biological materials. To date, these determinations are generally facilitated through the use of radiological, fluorescent or enzymatic tags. None of these methods have successfully dealt with elemental tagging of biologically active materials, for example immunoglobulins, aptamers or antigens, and analytes followed by detection using atomic mass or optical spectrometry.

The methods used to date have included (1) elemental tagging in immunoassays, (2) elemental tagging using radioisotopes, (3) elemental tagging to enhance fluorescence, (4) immunological detection of elemental species without tagging, and (5) direct elemental tagging for cell uptake studies. We will review each of these areas in turn.

Elemental Tagging in Immunoassays

Wang 1984 (U.S. Pat. No. 4,454,233) disclosed the possibility of utilizing a mass spectrometer as a means of immunoassay detection. Wang's method required a cumbersome preliminary set of steps to first prepare a tagged 'mobile unit' which was then conjugated to an antibody/antigen. In the preferred embodiment, the 'mobile unit' was comprised of a latex particle embedded with heavy tagging elements such as Fe, Ni, Cu and Co. Among Wang's reasons for utilizing 'mobile units' were: (1) easy separation of bound reactant from unbound reactant, (2) simultaneous detection of many antigen/antibody complexes owing to the small size of mobile units, and (3) possible utilization of 'unstable' or 'reactive' tags, as tags embedded in the latex would not interfere with the reaction. Wang's method has apparently not been accepted for immunoassay detection.

Immunoassay detection using element tagged immunoglobulins and antigens has also been possible using colloidal gold or extremely small beads of gold (several nanometers in diameter), for example NANOGOLD™ particles. Van Banchet and Heppelmann (1995), Wagenknecht et al. (1994), and Wenzel and Baumeister (1995) used colloidal gold to visualize protein structure in the cell and to detect receptor-ligand binding by electron microscopy. However, these assays suffer from lack of quantitation capabilities.

Element tagging has also been used in electrochemical immunoassays followed by polarographic detection of the generated complexes based on the catalytic conversion of a substrate by labeled metal ion or the anodic current of metal labeling Qiu and Song (1996). Similar to the preceding example, the assay lacked quantitation capabilities.

Thus, although elemental tagging has been used in immunoassays, the tagging methods have been cumbersome or were ineffective at quantitation.

Elemental Tagging Using Radioisotopes

Historically, the most common use of elemental tagging has been the use of radioactive elements. While radioassays remain the method of choice due to their exceptional sensitivity to low levels of analyte, their general use is limited by the restrictions in dealing with radioactive materials.

Elemental Tagging to Enhance Fluorescence

Recently, elemental tagging has been used to enhance luminescence of fluorescent tags. U.S. Pat. No. 4,637,988 to Hinshaw et al., describes the use of lanthanide metals complexed with fluorescent compounds and chelating agents, that can be used in specific binding assays. U.S. Pat. No. 5,958,783 to Josel et al. describes the use of metal complexes with a charged linker as luminescent groups in fluorescence-based or electrochemiluminescence-based assays.

However, these fluorescent tagging methods suffer from the disadvantages associated with their relatively low sensitivity and resulting problems with quantitative analysis in samples containing low concentrations of target molecules. As well, fluorescence-based methods are limited to the analysis and quantification of only one or at most a few target substances per assay.

Immunological Detection of Elemental Species

Blake et al. (1998) and Darwish and Blake (2001) disclosed a method of detection and quantitation of elemental species by complexing elemental species with antibodies that recognize elemental species, using antibodies conjugated with fluorescent tags. However, as outlined above, fluorescence based assays suffer from low sensitivity and are limited to one or a few targets per assay.

Direct Elemental Tagging in Conjunction with Gel Electrophoresis

Binet et al. (2001) disclosed a method of determining untagged proteins by separation using gel electrophoresis, followed by laser ablation of the separated spots and detection using mass spectrometry. However, this method has been limited to molecules that are naturally detectable by spectrometry.

Wind et al. (2001), Nagaoka and Maitani (2000) and Baldwin et al. (2001) used chromatography to separate proteins, followed by detection using mass spectrometry. Similarly, Chen et al, 2000 incorporated isotopic tags of $^{13}C$, $^{15}N$ and $^{2}H$ in proteins before chromatographic separation and detection using organic mass spectrometry. However, separation with chromatography is an added step, which can be onerous.

Thus, if one does not tag, one is limited to what is being assayed and using chromatography for separation adds a step to the process.

Direct Elemental Tagging for Cell Uptake Studies

Martin de Llano et al. (1996) and Martin de Llano et al. (2000), disclosed a method of visualizing and measuring the uptake of low density lipoprotein (LDL) tagged with colloidal gold by cells using electron microscopy and mass/atomic spectrometry. However, due to the use of colloidal particles, the difficulty in purifying labeled LDL, and the heterogeneity of cell assay systems, absolute quantitation was not necessary nor was it achieved.

Thus, various methods have been developed for visualizing and analyzing element tagged biologically active compounds. However, they have innate limitations, ranging from handling radioactive waste, to low sensitivity with fluorescence based assays, to detection only capabilities, and to cumbersome preparation or separation steps.

Various kits are currently in use for the detection and measurement of analytes. These kits contain radiological, fluorescent, or enzymatic reagents and are used in conjunction with detection instruments capable of measuring absorbance, luminescence, fluorescence, chemiluminescence, or radioactivity. However, none of these kits or methods have successfully dealt with the detection and measurement of element tagged biologically active materials and analytes, in particular immunoglobulins, aptamers, and antigens, followed by detection and measurement using an atomic mass or optical spectrometer.

Reagents (not currently sold in a kit format) containing element tagged immunoglobulins are commercially available (NanoProbes). In these reagents, the immunoglobulins are directly bound with colloidal gold or extremely small beads of gold (eg. NANOGOLD™ particles, which are 1.4 nm in diameter) and are currently used for in situ hybridization, electron microscopy and immunohistochemistry. In this manner, Segond von Banchet and Heppelmann (1995) and Wagneknecht et al. (1994) used colloidal gold to visualize protein structure in the cell and to detect receptor-ligand binding by electron microscopy. In another element-tagged method, Leuvering et al. (1982) have suggested using large elemental particles (with a size varying from 10-100 nm) coated either directly on immunological components or on inert polymer linkers and using spectrophotometric detection to analyze reactions. However, both of these assays suffer from lack of quantitation capabilities.

Recently, in immunoassay kits, elemental tags have been used to enhance the luminescence of fluorescent tags of immunoglobulins. Hinshaw et al. (1987) describe the use of lanthanide metals complexed with fluorescent compounds and chelating agents that can be used in specific immunoassays. Josel et al. (1990) describe the use of metal complexes with a charged linker as luminescent groups in fluorescence-base or electrochemiluminescence-based assays. However, these fluorescent lanthanide tag kits suffer from the disadvantages associated with their relatively low sensitivity and resulting problems with quantitative analysis in samples containing low concentrations of target molecules. As well, fluorescence-based methods are limited to the analysis and quantitation of only one or at most a few target substances per assay.

Several companies have designed kits for cytokine quantitation that contain radiological, fluorescent, or enzymatic reagents. For example, PerkinElmer (WALLAC DELFIA™ Assay kits), BD Biosciences (OptEIA ELISA™ kits), Pierce Biotechnology Inc. (SEARCHLIGHT HUMAN CYTOKINE™ array), R&D systems (QUANTIKINE ELISA™ kits) and various partners of Luiminex (e.g. R&D systems, Fluorokine kits) produce kits for cytokine quantitation. However, these kits are limited to either detecting only one cytokine or several (4-9) over a limited dynamic range with problems of fluorescence or chemiluminescence overlapping inhibiting sensitivities.

An enormous potential exists for the development of very simple biological assays and kits that take advantage of capabilities offered by elemental tagging coupled with elemental detection using a mass or optical spectrometer. Mass and optical spectrometry offer high sensitivity, accurate quantitation and a wide dynamic range. The use of elements to label biologically active material allows construction of an enormous number of distinguishable tags.

This invention involves bridging the science of biology, and in particular immunology, with analytical atomic mass spectrometry. The invention offers an easy and simple means of tagging biological molecules. Further, it offers excellent detection capabilities, equaling (or surpassing) the sensitivity of radioassays. It offers the safety of florescence based assays, and the added feature of an enormous number of available tags, with the possibility of simultaneous detection of numerous biological complexes. In addition, completed affinity assays can be stored indefinitely and the handling of the reacted tagged complexes can be crude, as the integrity of the chemical complex need not be preserved in assaying the element.

SUMMARY OF THE INVENTION

The last two decades have seen the improvement of elemental analysis due to the development of the inductively coupled plasma (ICP) source using mass or optical spectrometry. This has resulted in ultra sensitive spectrometers with high matrix tolerance and means of resolving isotopic and spectral interferences. The present invention has coupled the developments in this field with the continuing need to provide rapid and precise detection and measurement in biological assays.

In its broad aspect, the present invention provides a simple method of tagging biologically active materials, and detecting and measuring the reactant complexes by an atomic mass or optical spectrometer. Variations of the invention include detection and measurement of elemental species by complexing antibodies or aptamers to elemental species, and detection and quantitation of an analyte by tagging the analyte directly. The invention also provides kits comprising reagents for the detection and measurement of tagged biologically active materials and tagged competition analytes.

In addition, the present invention allows one to use a large array of elemental tags to allow the simultaneous or sequential detection and measurement of biologically active material. This is known as "multiplexing".

According to one aspect of the present invention, there is provided a method for the detection and measurement of an element in a sample, where the measured element is a tag on a biologically active material that binds with one of an analyte and analyte complex, comprising: i) combining the tagged biologically active material with one of the analyte and analyte complex, ii) separating bound tagged biologically active material from unbound tagged material, and iii) detecting and measuring the bound tag elements by one of an atomic mass and optical spectrometer having a source of ions or atomic ions.

According to another aspect of the present invention there is provided a method for the detection and measurement of an element in a sample, where the measured element is a tag on a biologically active material that binds with one of an analyte and analyte complex, comprising: i) combining the biologically active material with one of the analyte and analyte complex, wherein the biologically active material binds a transition element, ii) introducing the transition element to the sample, and iii) detecting and measuring the element by one of an atomic mass and optical spectrometer having a source of ions or atomic ions.

According to another aspect of the present invention, there is provided a method for the detection and measurement of an element in a sample, where the measured element is a tag on a biologically active material that binds with an analyte in the sample, comprising: i) directly tagging the biologically active material with a transition element, ii) combining the tagged biologically active material with the analyte in the sample where the biologically active material binds with the analyte, iii) separating bound tagged biologically active material from unbound tagged material, and iv) detecting and measuring the bound tag elements by one of an atomic mass and optical spectrometer having a source of atoms or atomic ions.

According to another aspect of the present invention, there is provided a method for the detection and measurement of an element in a sample, where a primary biologically active material binds with an analyte in the sample, and the measured element is a tag on a secondary biologically active material that binds to the primary biologically active material, comprising: i) combining the primary biologically active material with the analyte in a sample, where the primary biologically active material binds with the analyte, ii) separating bound biologically active material from unbound biologically active material, iii) directly tagging the secondary biologically active material with a transition element, iv) introducing the tagged secondary biologically active material into the sample where the secondary biologically active material binds with the primary biologically active material, v) separating bound tagged biologically active material from unbound tagged material, and vi) detecting and measuring the bound tag elements by one of an atomic mass and optical spectrometer having a source of atoms or atomic ions.

According to another aspect of the present invention, there is provided a method for the detection and measurement of an element in a sample, where a primary biologically active material binds with an analyte in the sample, and a secondary biologically active molecule binds with the primary biologically active material, and the measured element is a tag on a tertiary biologically active material that binds to the secondary biologically active material, comprising: i) combining the primary biologically active material with the analyte in a sample, where the primary biologically active material binds with the analyte, ii) separating bound biologically active material from unbound biologically active material, iii) introducing the secondary biologically active material in the sample, where the secondary biologically active material binds with the primary biologically active material, iv) separating bound biologically active material from unbound biologically active material, v) directly tagging the tertiary biologically active material with a transition element, vi) introducing the tagged tertiary biologically active material into the sample where the tagged tertiary biologically active material binds with the secondary biologically active material, vii) separating bound tagged biologically active material from unbound tagged material, and viii) detecting and measuring the bound tag elements by one of an atomic mass and optical spectrometer having a source of atoms or atomic ions.

According to another aspect of the present invention, there is provided a method for the detection and measurement of an element of an elemental species in a sample, where a biologically active material specific to the elemental species binds to the elemental species, comprising: i) introducing the biologically active material into the sample, ii) separating the biologically active material bound elemental species complexes from the sample, and iv) detecting and measuring an element of the elemental species contained in the removed complexes by one of an atomic mass and optical spectrometer having a source of atoms or atomic ions.

According to another aspect of the present invention, there is provided a method for the detection and measurement of an element in a sample including an elemental species, where the measured element is a tag on an antibody specific to the elemental species, comprising: i) tagging the antibody with a transition element, ii) introducing the tagged antibody into the sample where the tagged antibody binds with the elemental species, iii) separating tagged antibody bound elemental species from the sample, and iv) detecting and measuring an element contained in the removed complexes by one of an atomic mass and optical spectrometer having a source of atoms or atomic ions. Variations of this aspect include measuring and detecting the element of the elemental species and measuring and detecting both the tag element and element of the elemental species.

According to another aspect of the present invention, there is provided a method for the detection and measurement of an element in a sample, where the measured element is a tag on an analyte in a sample, comprising: i) tagging the analyte with a transition element, ii) electrophorescing the sample containing the tagged analyte, and iii) detecting and measuring the tagged analyte by one of an atomic mass and optical spectrometer having a source of atoms or atomic ions.

According to another aspect of the present invention, there is provided a method for the detection and measurement of an element in a sample where the measured element is a tag on a biologically active material that binds with an analyte in a sample, comprising: i) binding the analyte with a biologically active material, wherein the biologically active material binds a transition element, ii) electrophorescing the sample containing the bound analyte, iii) introducing the transition element to the electrophoresced sample, and iv) detecting and measuring the element by one of an atomic mass and optical spectrometer having a source of atoms or atomic ions.

According to another aspect of the present invention, there is provided a method for the detection and measurement of an element in a sample, where the measured element is a tag on a biologically active material that binds with an analyte in a sample, comprising: i) binding the analyte with the biologically active material, wherein the biologically active material binds a transition element, ii) introducing the transition element to the sample, wherein the element tags the biologically active material, and iii) detecting and measuring the element by one of an atomic mass and optical spectrometer having a source of atoms or atomic ions. A preferred embodiment of this aspect is a method where the analyte is a cell.

According to another aspect of the present invention, there is provided a method for the detection and measurement of an element in a sample, where the measured element is a tag on a biologically active material that binds with an analyte in a sample, comprising: i) tagging the biologically active material with a transition element, ii) electrophorescing the sample containing the analyte, iii) introducing the tagged biologically active material into the electrophoresced sample containing the analyte, and iv) detecting and measuring the element by one of an atomic mass and optical spectrometer having a source of atoms or atomic ions.

According to another aspect of the present invention, there is provided a method for the detection and measurement of an element in a sample, where a primary biologically active material binds with an analyte in the sample, and the measured element is a tag on a secondary biologically active material that binds to the primary biologically active material, comprising: i) electrophorescing the sample containing the analyte, ii) introducing the primary biologically active material into the electrophoresced sample where the primary biologically active material binds with the analyte, iii) tagging the secondary biologically active material with a transition element, iv) introducing the tagged secondary biologically active material into the electrophoresced sample, where the tagged secondary biologically active material binds with the primary biologically active material, and v) detecting and measuring the element by one of an atomic mass and optical spectrometer having a source of atoms or atomic ions.

According to a preferred aspect of the present invention, there is provided a method of measurement and detection of any of the aspects described above, wherein the tagged biologically active material is a commercially available product.

According to another preferred aspect of the present invention, there is provided a method of measurement and detection of any of the aspects described above, wherein the source of atoms or atomic ions is selected from a group consisting of inductively coupled plasma, graphite furnace, microwave induced plasma, glow discharge, capacitively coupled plasma, electrospray, MALDI and corona.

According to another preferred aspect of the present invention, there is provided a method of measurement and detection of any of the aspects described above, wherein the source of atoms or atomic ions is an inductively coupled plasma source.

According to another preferred aspect of the present invention, there is provided a method of measurement and detection of any of the aspects described above, wherein the step of detecting and measuring uses an optical spectrometer or a mass spectrometer.

According to another preferred aspect of the present invention, there is provided a method of measurement and detection of any of the aspects described above, wherein the element is an isotope or ion.

According to another preferred aspect of the present invention, there is provided a method of measurement and detection of any of the aspects described above, wherein the element is selected from a group consisting of the noble metals, lanthanides, rare earth elements, gold, silver, platinum, rhodium, iridium and palladium.

According to another preferred aspect of the present invention, there is provided a method of measurement and detection of any of the aspects described above, wherein the step of tagging involves covalently coupling the element to one of the biologically active material and analyte.

According to another preferred aspect of the present invention, there is provided a method of measurement and detection of any of the aspects described above, wherein the biologically active material is selected from a group consisting of an antibody, Fab or Fab∝ fragment, aptamer, antigen, hormone, growth factor, receptor, protein and nucleic acid.

According to another preferred aspect of the present invention, there is provided a method of measurement and detection of any of the aspects described above, wherein the tag includes more than one element.

According to another preferred aspect of the present invention, there is provided a method of measurement and detection of any of the aspects described above, wherein the tag includes more than one isotope.

According to another preferred aspect of the present invention, there is provided a method of measurement and detection of any of the aspects described above, wherein the tag includes more than one atom of an isotope.

According to another preferred aspect of the present invention, there is provided a method of measurement and detection of any of the aspects described above, wherein the tag includes a different number of atoms of each isotope.

According to another preferred aspect of the present invention, there is provided a method of measurement and detection described in any of the aspects above comprising an additional step of introducing two or more biologically active materials or analytes having distinguishable elemental tags into a sample of interest for simultaneous determination.

According to another preferred aspect of the present invention, there is provided a method of measurement and detection described in any of the aspects above comprising an additional step of sample introduction, wherein the sample introduction includes laser ablation.

According to another preferred aspect of the present invention, there is provided a method of measurement and detection described in any of the aspects above wherein the sample introduction includes laser ablation of polyacrylamide or agarose gels or nitrocellulose or PVDF (polyvinylidene fluoride) or hydrophilic polypropylene (GHP, GH Polypro) membranes containing biologically active materials or analytes tagged by at least one element.

According to another preferred aspect of the present invention, there is provided a method of measurement and detection described in any of the aspects above wherein the sample introduction includes laser ablation of polyacrylamide or agarose gels or nitrocellulose or PVDF or hydrophilic polypropylene membranes containing biologically active materials or analytes tagged by atoms of at least one element having an unnatural isotopic composition.

According to another preferred aspect of the present invention, there is provided a method of measurement and detection described in any of the aspects above wherein the sample introduction includes laser ablation of animal tissue samples.

According to another preferred aspect of the present invention, there is provided a method of measurement and detection described in any of the aspects above wherein the sample introduction includes laser ablation of cell cultures or laser ablation of the biologically active material or the analyte.

According to another aspect of the present invention, there is provided a system of detection and measurement of molecules according to any of the aspects described above.

According to another aspect of the present invention, there is provided the use of one of an atomic mass and optical spectrometer for the detection and measurement an element described in any of the aspects above.

According to another aspect of the present invention, there is provided the use of one of an atomic mass and optical spectrometer for the detection and measurement of an elemental species described in any of the aspects above.

According to another aspect of the invention, there is provided a kit for the detection and measurement of a transition element in a sample, where the measured transition element is a tag on a biologically active material that binds with at least one of an analyte and analyte complex, comprising a tag comprising a transition element for directly tagging a biologically active material; and instructions for i) directly tagging a biologically active material; ii) combining the tagged biologically active material with at least one of an analyte and analyte complex under conditions in which the tagged biologically active material binds with at least one of the analyte and analyte complex, iii) separating bound tagged biologically active material from unbound material, and iv) detecting and measuring the bound tag elements using an atomic mass or optical spectrometer having a source of atoms or atomic ions.

According to another aspect of the invention, there is provided a kit for the detection and measurement of a transition element in a sample, where the measured transition element is a tag on a competition analyte, comprising a tag comprising a transition element for directly tagging a competition analyte and instructions for i) directly tagging the competition analyte, (ii) combining the tagged competition analyte with at least one of the analyte and analyte complex, where the tagged competition analyte and at least one of the analyte and anlayte complex are in competition for a binding site, iii) separating bound tagged competition analyte from the unbound tagged competition analyte, and iv) detecting and measuring the tag element on the bound competition analyte by an atomic mass or optical spectrometer having a source of atoms or atomic ions, wherein the detection and measurement of the tag element on the bound competition analyte is related to the detection and measurement of at least one of the analyte and analyte complex.

According to another aspect of the invention, there is provided a kit for the detection and measurement of a transition element in a sample, where the measured transition element is a tag on a biologically active material that binds with at least one of an analyte and analyte complex comprising, a biologically active material directly tagged with a transition element, and instructions for i) combining the tagged biologically active material with at least one of an analyte and analyte complex under conditions in which the tagged biologically active material binds with at least one of the analyte and analyte complex, ii) separating bound tagged biologically active material from unbound material, and iii) detecting and measuring the bound tag elements using an atomic mass or optical spectrometer having a source of atoms or atomic ions.

According to another aspect of the invention, there is provided a kit for the detection and measurement of a transition element in a sample, where the measured transition element is a tag on a competition analyte, comprising, a competition analyte tagged with a transition element, and instructions for i) combining the tagged competition analyte with at least one of the analyte and analyte complex, where the tagged competition analyte and at least one of the analyte and analyte complex are in competition for a binding site, ii) separating bound tagged competition analyte from the unbound tagged competition analyte, and iii) detecting and measuring the tag element on the bound competition analyte by an atomic mass or optical spectrometer having a source of atoms or atomic ions, wherein the detection and measurement of the tag element on the bound competition analyte is related to the detection and measurement of at least one of the analyte and analyte complex.

The kits may also comprise capture molecules that bind the analyte, analyte complex or competition analyte. The kits may also include solid support means, wherein the solid support means comprises binding sites for the analyte or capture molecules, and may include microwell plates and beads. Further, the capture molecules may include antibodies and aptamers.

The kits may also include standards, dilution buffers, elution buffers, wash buffers and assay buffers.

The element used in the kits is selected from a group consisting of the noble metals, lanthanides, rare earth elements, gold, silver, platinum, rhodium, iridium and palladium. Further, the element may include more than one element, isotope or atom of an isotope and may include a different number of atoms of each isotope.

The kits may also comprise two or more biologically active materials or competition analytes having distinguishable elemental tags for simultaneous determination of two or more analytes. The kits may include reagents and instructions for two or more aspects of the present invention.

Another aspect of the invention is to provide a kit for the detection and measurement of an element in a sample, where the measured element is a tag on an analyte in a sample, comprising, reagents for tagging the analyte with a transition element, reagents for running a sample containing the tagged analyte on an electrophoresces gel, and instructions for i) tagging the analyte with a transition element, ii) running the sample containing the tagged analyte on an electrophoresces gel, and iii) detecting and measuring the element by an atomic mass or optical spectrometer having a source of atoms or atomic ions.

Another aspect of the invention is to provide a kit for the detection and measurement of an element in a sample, where the measured element is a tag on a biologically active material that binds with at least one of an analyte and analyte complex, comprising, a biologically active material that binds with at least one of the analyte and analyte complex, a transition element, and instructions for i) combining the biologically active material with at least one of the analyte and analyte complex, wherein the biologically active material binds a transition element, ii) introducing the transition element to the sample, and iii) detecting and measuring the element using an atomic mass or optical spectrometer having a source of atoms or atomic ions.

The invention also provides a kit for the detection and measurement of an element of an elemental species in a sample where an antibody specific to an elemental species binds to the elemental species, comprising, a biologically active material specific to the elemental species; and instructions for i) introducing the biologically active material into the sample, ii) separating the biologically active material bound elemental species complexes from the sample, and iii) detecting and measuring an element of the elemental species contained in the removed complexes using an atomic mass or optical spectrometer having a source of atoms or atomic ions.

Another aspect of the invention is to provide a method for the detection and measurement of a transition element in a sample, where the measured transition element is a tag on an aptamer that binds with an analyte, comprising combining a tagged aptamer with the analyte, where the tagged aptamer binds with the analyte, separating bound tagged aptamer from unbound tagged aptamer, and detecting and measuring the transition element by an atomic mass or optical spectrometer having a source of ions or atomic ions.

Another aspect of the invention is to provide a method for the detection and measurement of an element in a sample, where the measured element is a tag on an aptamer that binds with an analyte, comprising, combining the aptamer with the analyte, introducing a transition element to the combined aptamer and analyte, wherein the transition element binds with the aptamer, and detecting and measuring the transition element by an atomic or optical spectrometer having a source of ions or atomic ions.

Another aspect of the present invention is to provide a method for the detection and measurement of an element in a sample, where the measured element is a tag on a competition analyte, comprising combining a tagged competition analyte with at least one of an analyte and analyte complex, where the tagged competition analyte and at least one of the analyte and anlayte complex are in competition for a binding site, separating bound tagged competition analyte from the unbound tagged competition analyte, and detecting and measuring the transition element on the bound competition analyte by an atomic mass or optical spectrometer having a source of atoms or atomic ions, wherein the detection and measurement of the transition element is related to the detection and measurement of at least one of the analyte and analyte complex. The binding site may be located on a capture molecule.

Other features and advantages of the present invention will become apparent from the following detailed description. It should be understood, however, that the detailed description and the specific preferred embodiments of the invention are given by way of illustration only, since various changes and modifications within the spirit and scope of the invention will become apparent to those skilled in the art from this detailed description.

BRIEF DESCRIPTION OF THE FIGURES

The invention will now be described in relation to the drawings in which.

DETAILED DESCRIPTION OF THE INVENTION

Definitions

Figure 1:
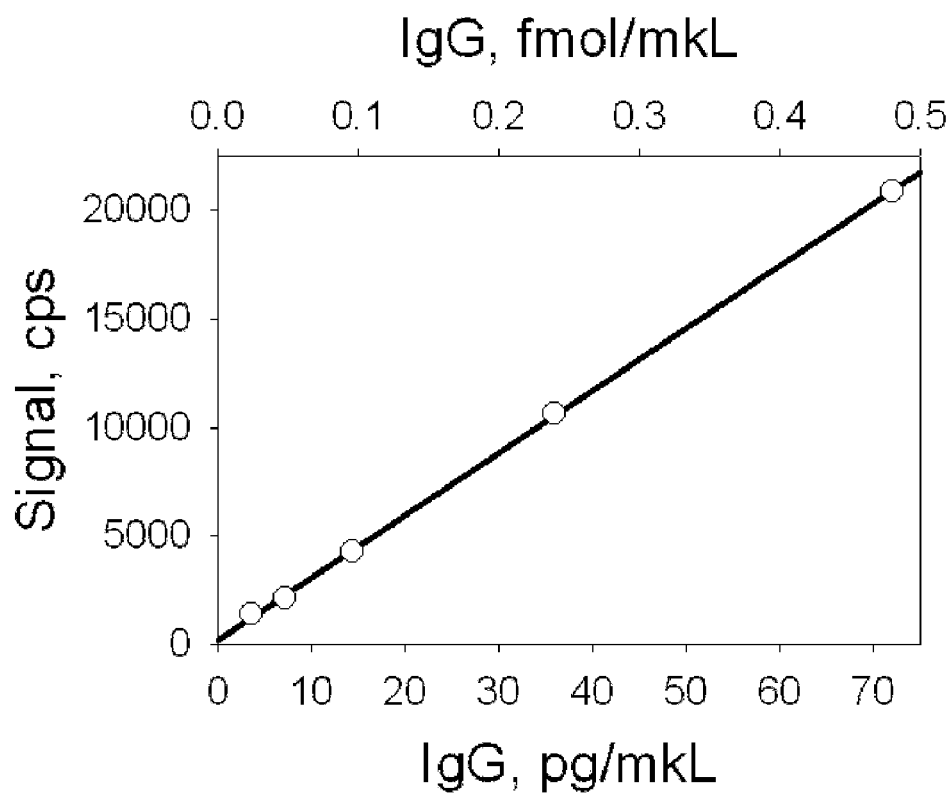
FIG. 1 is a graph illustrating a calibration curve obtained by dilutions of human IgG and immunoreaction with the gold-labeled anti-human antibody with detection and quantitation using ICP-MS.

As used in this application:

"analyte" means any substance being identified or measured in an analysis, and includes but is not limited to elemental species, element species chelate complexes; cells, viruses, subcellular particles; proteins including more specifically antibodies, immunoglobulins, antigens, ligands, lipoproteins, glycoproteins, peptides, polypeptides; nucleic acids including DNA and RNA; and including peptidic nucleic acids; oligosaccharides, polysaccharides, lipopolysaccharides; cellular metabolites, haptens, hormones, pharmacologically active substances, alkaloids, steroids, vitamins, amino acids and sugars.

"analyte complex" means an analyte bound to other molecules or biologically active materials.

"animal" means all members of the animal kingdom.

"aptamer" means any polynucleotide molecule (for example, DNA or RNA molecule containing natural or synthetic nucleotides) that has the ability to bind other molecules. For example, aptamers have been selected which bind nucleic acids, proteins, small organic components and even entire organisms.

"atomic mass spectrometer" means a mass spectrometer that generates atomic ions, and detects atomic ions based on the mass/charge ratio.

"biologically active material(s)" means any biological substance found in nature or synthetic, and includes but is not limited to cells, viruses, subcellular particles; proteins including more specifically antibodies, immunoglobulins, antigens, lipoproteins, glycoproteins, peptides, polypeptides, protein complexes (including complexes involving ligands, receptors, or small molecules); nucleic acids including DNA and RNA, aptamers, and including peptidic nucleic acids; oligosaccharides, polysaccharides, lipopolysaccharides, cellular metabolites, haptens, hormones, pharmacologically active substances, alkaloids, steroids, vitamins, amino acids and sugars.

"capacitively coupled plasma" (CCP) means a source of ionization in which a plasma is established by capacitive coupling of radiofrequency energy at atmospheric pressure or at a reduced pressure (typically between 1 and 500 Torr) in a graphite or quartz tube.

"capture molecule" means any molecule capable of binding with an analyte.

"competition analyte" means a purified form of the tagged analyte of interest. The tag may be a radioisotope, fluorescence, enzyme or an element. A competition analyte is used in competition assays in which the analyte of interest in a sample is quantitated by determining the concentration of tagged competition analyte that successfully binds to the analyte binding sites provided in the assay after exposure to the sample containing the analyte of interest.

"corona" means a source of ionization in which a conductor (typically a needle) is provided a voltage relative to a counter electrode surface (typically containing an ion sampling aperture) such that the voltage gradient exceeds a critical value to cause ionization of the surrounding gas, but not sufficient to cause sparking.

"cytokine" means a regulator. In nature, cytokines are usually comprised of soluble proteins and peptides that may be secreted by one cell for the purpose of altering its own function (autocrine effect), those of adjacent cells (juxtacrine effect), those of near-by cells (paracrine effect), or events occurring in the extracellular environment.

"elemental species" means a molecule containing a metal bound to another atom or group of atoms. For example, selenite ($SO_3^{-2}$), selenate ($SO_4^{-2}$), methylselenocysteine and selenomethionine are elemental species of selenium.

"directly tagged" includes any of the methods of tagging described herein, including but not limited to covalently and coordinatively bound transition elements, but excluding tags made up of encapsulated transition elements embedded in latex.

"element tagged" means a molecule tagged with a transition element, including a noble metal or lanthanide.

"elemental tag" means any transition element, including a noble metal or lanthanide, used to tag the biologically active material or analyte.

"electrospray" means a source of ionization in which a liquid sample is nebulized from a tube due to the sufficiently high potential applied, which also provides a charge to the droplet, and in which the resultant charged droplet evaporates and fragments yielding small charged droplets or charged molecular ions.

"Fab" means the antigen binding fragment of an antibody obtained by papain reaction with immunoglobulin.

"Fab'" means the antigen binding fragment of an antibody. Fab' fragments are usually obtained by pepsin reaction with immunoglobulin, followed by cleavage of two disulfide bonds.

"Glow discharge" (GD) means a source of ionization in which a discharge is established in a low pressure gas (typically between 0.01 and 10 Torr), typically argon, nitrogen or air, by a direct current (or less commonly radiofrequency) potential between electrodes.

"graphite furnace" means a spectrometer system that includes a vaporization and atomization source comprised of a heated graphite tube. Spectroscopic detection of elements within the furnace may be performed by optical absorption or emission, or the sample may be transported from the furnace to a plasma source (e.g. inductively coupled plasma) for excitation and determination by optical or mass spectrometry.

"inductively coupled plasma"(ICP) means a source of atomization and ionization in which a plasma is established in an inert gas (usually argon) by the inductive coupling of radiofrequency energy. The frequency of excitation force is in the MHz range.

"lanthanide" means any element having atomic numbers 58-71. They are also called rare earth elements.

"MALDI" means a source of ionization (Matrix Assisted Laser Desorption Ionization) in which ions are produced from a sample mixed with a matrix (typically analyzed in crystalline form) by exposure to laser irradiation, typically at low pressure "mass spectrometer" means an instrument for producing ions in a gas and analyzing them according to their mass/charge ratio.

"microwave induced plasma" (MIP) means a source of atomization and ionization in which a plasma is established in an inert gas (typically nitrogen, argon or helium) by the coupling of microwave energy. The frequency of excitation force is in the GHz range.

"multiplexing" means using more than one elemental tag for the simultaneous or sequential detection and measurement of biologically active material.

"noble metal" means any of several metallic elements, the electrochemical potential of which is much more positive than the potential of the standard hydrogen electrode, therefore, an element that resists oxidation. Examples include palladium, silver, iridium, platinum and gold.

"optical spectrometer" means an instrument calibrated to measure either wavelength of light or the refractive index of a prism, and includes atomic emission and atomic absorption spectrometers.

"plasma source" means a source of atoms or atomic ions comprising a hot gas (usually argon) in which there are (approximately) equal numbers of electrons and ions, and in which the Debye length is small relative to the dimensions of the source.

"primary biologically active material" means any molecule that binds to the analyte.

"rare earth metals" means any element having atomic numbers 58-71. The are also called "lanthanides'.

"sample" means any composition of liquid, solid or gas containing or suspected of containing an analyte.

"secondary biologically active material" means any molecule that binds to the analyte or primary biologically active material.

"tertiary biologically active material" means any molecule that binds to the analyte, the primary biologically active material or the secondary biologically active material.

"transition element" means any element having the following atomic numbers, 21-29, 39-47, 57-79, and 89. Transition elements include the rare earth elements, lanthanides and noble metals. (Cotton and Wilkinson, 1972, pages 528-530).

There are a number of aspects to the present invention.

The first aspect involves labeling of biologically active material which binds to an analyte in a sample. Most often, the biologically active material would be an immunoglobulin, aptamer or antigen. The element is detected by an atomic mass or optical spectrometer having a source of atoms or atomic ions. Examples 1, 2, 3, 4, 5, 6, 7, 8, 10, 14, 15 and 16 are examples of this aspect of the invention.

The individual steps involved in this first aspect of the invention are known to those skilled in the art but the coupling of assays with spectrometry is new and inventive. Each of the individual steps is described in Materials and Methods section of this application.

The benefits of this aspect of the invention are that: (1) it allows for the detection of minute quantities of analyte, (2) it allows for multiplexing, saving time, resources and providing for a better analysis of the sample, (3) the analysis is very rapid as there is no need to wait for enzymatic reactions, and measurement time by ICP-OES/MS is shorter than radiological tag measurement, (4) it has a large dynamic range, (5) radioisotopes are not required, producing a safe work environment and avoids toxic waste, and (6) the reacted complex does not need to be preserved, allowing the use of acidic media to degrade the complex and stabilize the element in solution and thereby increasing the period of storage of the sample before analysis.

The second aspect involves the determination of elemental species. In cases where mass spectrometry cannot differentiate elemental species, the use of antibodies or aptamers to detect elemental species coupled with mass spectrometry allows for their differentiation. Examples 11, 12 and 13 describe this aspect of the invention in more detail. In this aspect, as show in Example 13, multiplexing can be used. Again, the benefits of this aspect are that: (1) it allows for the detection of minute quantities of analyte, (2) it allows for multiplexing, (3) the analysis is very rapid, (4) there is a large dynamic range, (5) one can avoid the use of radioisotopes, (6) the reacted complexes do not need to be preserved, and (7) chromatographic separation is not required, which speeds up and simplifies the analysis.

The third aspect is the direct labeling of the analyte. The individual steps involved in this third aspect are known to those skilled in the art, but direct labeling coupled with mass spectrometry is new and inventive. Example 17 describes this third aspect of the invention. A variation of this aspect is described in Example 9. Again, the benefits of this third aspect are that: (1) it allows for the detection of minute quantities of analyte, (2) it allows for multiplexing, (3) the analysis is very rapid, (4) there is a large dynamic range, (5) one can avoid the use of radioisotopes, (6) the reacted complexes do not need to be preserved, and (7) chromatographic separation is not required, which speeds up and simplifies the analysis.

The fourth aspect of the invention is the provision of kits comprising reagents for the detection and measurement of tagged biologically active materials and tagged competition analytes. For example, the kits may include reagents for the detection and measurement of cytokines. Elemental-tagged antibodies, aptamers or cytokines in conjunction with atomic mass or optical spectrometry have never been used to quantitate levels of cytokine in mixed biological samples.

The benefits of this aspect of the invention are many. The kits allow for an extremely sensitive assay, there is no over-lap in signal, there is a wide dynamic range (over 8 orders of magnitude), there is a large potential for multiplexing (up to 167 different isotopes are available), radioisotope handling is not required, and the kits can withstand long term storage. These benefits are discussed in detail below. The kits will be described with reference to kits for cytokine analysis, but it is understood that kits for the analysis by mass or optical spectrometry of any analyte are within the scope of the invention.

First, the ability to quantitate multiple cytokines simultaneously with an atomic mass or optical spectrometer is not subject to the same problems with over-lapping signal associated with fluorescence.

Second, due to lower backgrounds and enriched tags, the sensitivity of atomic mass or optical spectrometry in analyzing elemental tags, provides a tool that is more sensitive than existing methods. Both of these features allow the measurement of various cytokines in widely different concentrations which is desirable when assessing immunological phenotypes of patients before and after different therapies.

Third, being able to determine a plurality of cytokines in a single sample, means that less sample (e.g. blood, mucus, tissue, etc.) is required from each patient, which is always an advantage.

Fourth, element-tagged affinity assays can draw upon 167 different isotopes for tags which is far more than necessary for quantitating pools of cytokines, and this assay is therefore not limited not by the number tags that can be multiplexed. In comparison current kits manufactured that are designed for cytokine quantitation through use of radiological, fluorescent, or enzymatic reagents are limited to either detecting only one cytokine or several (4-9) over a limited dynamic range with problems of fluorescence/chemiluminescence signals overlapping and inhibiting sensitivities. Fluorescent systems that claim to multiplex more than ten cytokines are not simultaneous and rely on flow cytometry to separate signals, so that the fluorometric detector is only subjected to two fluorophores at a time. This adds to the time required to perform each assay as measurements are recorded bead by bead.

Fifth, the kits along with the methods provide a large dynamic range (over 8 orders of magnitude), which is not possible with either fluorescence or chemiluminescence. This feature is a benefit when quantifying multiple cytokines, where it is foreseeable that one cytokine may be expressed at low levels where another may be expressed in much greater concentration.

Finally, element-tagged affinity assays permit long-term storage prior to analysis. This is very advantageous, as instrument sharing or mechanical problems can create a backlog, which means that plates dependent on fluorescence, or chemiluminescence may suffer from faded signals and therefore inaccurate readings. Long-term storage allows for more flexibility in both time and location as reacted plates can even be shipped dry for elemental analysis at a different location.

For all aspects of the invention, it is understood that the biologically active material can be added to the analyte, or the analyte can be added to the biologically active material. Further, an analyte complex can be formed, by the binding of molecules to the analyte, as seen in the examples outlined below, in which a series of antibodies (primary, secondary, tertiary) can be conjugated to the analyte.

Tagging Elements

The choice of the element to be employed in the methods of the present invention is preferably selected on the basis of its natural abundance in the sample matrix under investigation. In order to achieve selectivity, specificity, the ability to provide reproducible results, and include appropriate standards for accurate quantitation, it is evident that the tagging element should be of low natural abundance. For example, in a preferred embodiment, the rare earth elements or gold can be used as tag materials. Yet, in another embodiment, an unusual isotope composition of the tag can be used in order to distinguish between naturally present elements in the sample and the tag material. In this case non-radioactive isotopes of, for example, iron, potassium, nickel or sodium can be successfully distinguished from naturally abundant isotopes employing the elemental analysis.

The size of an elemental tag (ratio of atoms which are detectable by means of the elemental analysis to the analyte complex) may be varied in order to produce the most consistent, sensitive and quantitative results for each analyte complex.

In a preferred embodiment of this invention, several conjugates can be used in one sample simultaneously providing that the tagging material was selected to be different in every assay. In this embodiment the preferred ICP-MS technique is used in order to quantify different tagging elements simultaneously or sequentially depending on the apparatus employed.

Although many applications of the present method will involve the use of a single elemental tag for each biologically active material (for example, antibody, aptamer or antigen) or analyte, it should be readily appreciated by those skilled in the art that a biologically active material (for example, an antibody, aptamer or antigen) or analyte may be tagged with more than one element. As there are more than 80 naturally occurring elements having more than 250 stable isotopes, there are numerous elements, isotopes and combinations thereof to choose from. For example, there are 20 distinguishable 3-atom tags that may be constructed from only 4 different isotopes, and one million distinguishable 15-atom tags that may be constructed from 10 different isotopes, or 70-atom tags that may be constructed from 5 different isotopes. Within limits prescribed by the need to have distinguishable tags when in combination, this will allow for simultaneous detection of numerous biologically tagged complexes. It is advantageous if the relative abundance of the tag elements is sufficiently different from the relative abundance of elements in a given sample under analysis. By "sufficiently different" it is meant that under the methods of the present invention it is possible to detect the target biologically active material (for example, antibody, aptamer or antigen) or analyte over the background elements contained in a sample under analysis. Indeed, it is the difference in inter-elemental ratios of the tagged biologically active material (for example, antibody, antigen or aptamer) or analyte and the sample matrix that can be used advantageously to analyze the sample.

It is feasible to select elemental tags, which do not produce interfering signals during analysis (i.e. do not have overlapping signals due to having the same mass). Therefore, two or more analytical determinations can be performed simultaneously in one sample. Moreover, because the elemental tag can be made containing many atoms, measured signal can be greatly amplified.

Detection of Metal Ions and Elemental Species

As was indicated above, an important application of the method of the present invention is the detection of metal in samples, such as toxic metals in environmental settings, including organisms, animals, and humans. Preferably, the invention detects metals in environmental settings. However, as is readily apparent to those skilled in the art, the toxicity of metals depends on the oxidation state, and often on the chemical structure of the elemental species. While an elemental detector, such as uses an ICP source, is able to determine the total quantity of an element in a sample it is generally unable to distinguish different species. There is an ongoing attempt to use different forms of chromatography to pre-separate the sample before the ICP, but this approach has been plagued with concern about the integrity of the sample, i.e., preservation of the oxidation state during sample preparation. The method of the present invention provides a means by which a long-standing problem of detecting speciation is overcome.

In a further embodiment of the present invention, there is provided a method of determining the concentration of a metal ion of interest, preferably toxic metals, more preferably in environmental/biological samples, comprising preparing a biologically active material (for example an antibody or aptamer) which is specific to a selected speciation state of a given toxic metal, reacting said antibody with a solution suspected of containing a toxic metal, and detection of the resulting complexes by application of ICP-MS. Methods for the preparation of an antibody which is specific to a selected oxidation state of a given toxic metal are known by those skilled in the art and are described, for examples, in Bosslet et al.(1999), Blake et al. (1998), and Bordes et al. (1999).

In a further embodiment of the present invention, an element-tagged biologically active material (for example, an element-tagged antibody or aptamer) is added to a sample containing a speciated element. The sample is split into two halves. The first half of the sample is analyzed for total speciated element. In the second half of the sample, the reacted complexes are separated from the unreacted. The tagging element and the speciated element are quantified in the reacted sample. The speciated element is also quantified in the unreacted sample. In this instance, the results will provide complementary data, and the fraction of the specific species in question will be determined.

As was also indicated above, an important application of the method of the present invention is the detection of elements of tags in samples by means of laser ablation of polyacrylamide gels where tagged molecules are separated by electrophoresis. Optionally, the sample can be run on an electrophoresis gel and then probed using element tagged biologically active materials, for example antibodies or aptamers. This application can be used in order to analyze biomolecules in gels or membranes rapidly without destroying the sample. Also, by employing microablation it is feasible to distinguish cancerous cells from normal cells on histological section of biopsy samples using element-tagged antibodies specifically attached to the markers of cancerous populations.

The following section describes the methods and materials required to carry out the following invention.

Methods and Materials

ICP-MS Techniques

Techniques using ICP-MS or OES can be applied for the purposes of this invention.

For example, in its latest realization it was described in Tanner el al.(2000a), Baranov et al. (1999), Tanner et al. (1999), Tanner et al. (2000b), and Bandura et al. (2000). This successful modification of ICP-MS includes the dynamic reaction cell, which is used in order to reduce isobaric interferences in atomic mass spectrometry. Briefly, the ICP-DRC-MS technique comprises a high temperature plasma in which the sample particles are atomized and ionized; vacuum interface which is designed to transport the plasma together with analyte ions from atmospheric pressure to vacuum; ion focusing optics; the dynamic reaction cell for chemical modification of the ion current and mass analyzing devise (quadrupole, TOF or magnetic sector). The sample is usually introduced to the plasma as a spray of droplets (liquid sample) or flow of particles (laser ablation of solid surfaces).

Sources of Atoms and Atomic Ions

The source of atoms or atomic ions can be produced from the following sources: inductively coupled plasma (ICP), graphite furnace, microwave induced plasma (MIP), glow discharge (GD), capacitively coupled plasma (CCP), electrospray, MALDI or corona.

Antibody Preparation

According to a preferred embodiment of the methods of the present invention, elementally tagged antibodies, or antibodies directed to a metal of interest are employed. Antibodies that bind a target of interest can be prepared using techniques known in the art such as those described by Kohler and Milstein (1975), Wakabayashi et al. (1990), Frackelton et al. (1985) and Gillis (1983), which are incorporated herein by reference. (See also Kennett, McKearn, and Bechtol (1980), and Harlow and Lane (1988), which are also incorporated herein by reference).

Within the context of the present invention, antibodies are understood to include monoclonal antibodies, polyclonal antibodies, antibody fragments (e.g., Fab, and $F(ab')_2$) and recombinantly produced binding partners. Antibodies are understood to be reactive against the target analyte if they bind to the target with an affinity of greater than or equal to $10^{-6}$ M.

Aptamer Preparation

According to a preferred embodiment of the methods of the present invention, elementally tagged aptamers directed to an anlayte are employed. Aptamers that bind a target of interest can be prepared using techniques known in the art such as those described in Ellington A D and Szostak J W. (1990);

Turek C and Gold L (1990); Robertson D L and Joyce G F (1990); Gold, L, Polisky, B, Uhlenbeck, O, and Yarus, M (1995); Szostak, J W (1995).

Tagging of Biologically Active Materials

Preferably, the tagging element is in the form of a nanoparticle, which is attached to a biologically active material, such as for example an antibody, without degrading its activity (tagged conjugate). Examples of techniques for coupling elemental tags to biologically active materials are well known to those skilled in the art. For example, Barlett, P. A. et al. (1978), describe a metal cluster compound ($Au_{11}$) having a core of 11 gold atoms with a diameter of 0.8 nm. The metal core of 11 gold atoms in the undecagold metal cluster compound is surrounded by an organic shell of $PAr_3$ groups. This metal cluster compound has been used to form gold immunoprobes, for example, by conjugating $Au_{11}$ to Fab' antibody fragments as well as other biological compounds.

Another metal cluster compound which has been used as a probe is NANOGOLD™. NANOGOLD™ has a metal core with 50-70 gold atoms (the exact number not yet being known but believed to be 67 gold atoms) surrounded by a similar shell of organic groups (PAr3) as undecagold. The metal core of NANOGOLD™ is 1.4 nm in diameter.

A more recent description of techniques for the preparation of biological tags, which may be used in the method of the present invention, is found in Hainfeld et al. (1996) (U.S. Pat. No. 5,521,289). Briefly Hainfeld et al. (1996) describes, among others, thiol gold clusters produced by forming an organic-gold complex by reacting a compound containing a thiol with gold in solution. A second equivalent is also added of the thiol compound. Finally the gold organic is reduced with $NaBH_4$ or other reducing agents and organometallic particles are formed. These have the general formula $Au_n$-$R._mR'_1$ . . . , where n, m, and 1 are integers, R and R' are organic thiols, (e.g., alkyl thiols, aryl thiols, proteins containing thiol, peptides or nucleic acids with thiol, glutathione, cysteine, thioglucose, thiolbenzoic acid, etc.). With two equivalents of organic thiol compound, clusters with gold cores ~1.4 nm are formed with many organics. The organic moiety may then be reacted by known reactions to covalently link this particle to antibodies, lipids, carbohydrates, nucleic acids, or other molecules to form probes. Mixtures of organic thiols may be used to provide mixed functionality to the clusters. These organo-gold clusters are stable to heating at 100 degrees C.

These organic thiol-gold preparations may also be made using similar processes with alternative metals to gold, e.g., platinum, silver, palladium and other metals, or mixtures of metal ions, e.g., gold and silver, resulting in mixed metal clusters. The metal clusters together with all other components of a sample are readily atomized and ionized in the high temperature ICP for subsequent MS or OES analysis.

Separation Techniques

According to one embodiment of the present invention, a tagged conjugate may be isolated for analysis by employing a filtration technique. For example, after incubation of an analyte with the tagged conjugate the sample undergoes filtering through a size separating centrifugal filter. Non-reacted tagged antibody together with other components of the sample mixture including non-reacted antigen pass through the filter into the filtrate. Complexes of analyte and antibody conjugate are left on the filter and after washing can be stabilized in acidic solution. Since the integrity of the sample (i.e. the chemical form) is not important after separation, the separated sample can be acidified/degraded/stabilized (for example in acidic media) and quantitative analysis is preferably carried out using the ICP-MS technique. The optimal concentrations of all reagents for each system should be determined in an initial criss-cross serial dilution experiment and the concentration of reagent being quantitated must lie within the dynamic range of the standard curve. As will be readily apparent to those skilled in the art, other techniques of separation of free substance or non-complexed proteins from complexed substance may be used, for examples, salting out, chromatography, electrophoresis, gel filtration, fractionation, absorption, polyacrylamide gel electrophoresis, agglutination, affinity separations, immunoassays, or combinations thereof.

Kits

Kits are provided for all aspects of this invention.

Kits are provided for the first aspect of the invention in which a biologically active material binds to an analyte in a sample. Examples 1, 2, 3, 4, 5, 6, 7, 8, 10, 14, 15 and 16 describe this aspect of the invention. The kits may include 1) tags comprising transition elements; 2) element-tagged biologically active materials (including antibodies, aptamers, antigens, or combinations of the above) or element-tagged competition analytes, 3) solid supports, for example microwell plate or beads and filter-plate, 4) analyte standards (i.e. analytes of known concentration, unlabeled in the sandwich and direct assays and element-labeled in the competition assays), 5) diluent buffers, 6) assay buffers, 7) wash buffers, 8) elution buffers and 9) protocols and instructions to carry out the detection and measurement of an element in a sample.

Each of these components is discussed below.

(1) The tags comprising transition elements as described above.

(2) The element-tagged biologically active material would preferably contain element tags that are biologically inert and uniform in both size (number of atoms) and isotopic purity. Preferably the tagging of the biologically active material involves the covalent attachment of elemental tags to the biologically active material at sites that minimize loss of activity. The element-tagged biologically active material may include any biologically active material, for example, antibodies, aptamers, or antigens.

In kits designed for competitive assays, competition analytes of interest are tagged with elements. The tags are preferably biologically inert and uniform in both size (number of atoms) and isotopic purity. Preferably they are water soluble, non-toxic, easily separated from a tagged material by known chromatographic or dialysis methods.

In the preparation of element-tagged biologically active materials or competition analytes, purification steps are required to separate free element tags from tagged biologically active materials or competition analytes. This may be done using size exclusion chromatography, affinity chromatography, filtration, or dialysis. The purity and quantity of the element-tagged biologically active materials or competition analytes can be analyzed through UV spectrophotometry or atomic mass or optical spectrometry. The affinity of the element-tagged biologically active materials and the element tagged-competition analytes to the target molecule is determined by test protocols of element-tagged immunoassay prior to sale of the kit.

(3) The assay may comprise solid supports such as microwell plates, beads columns, filters, membranes, gels, or sol-gel to support sandwich, direct, or competitive element-tagged affinity assays. The beads may comprise agarose, sepharose, polystyrene, or polymeric micro spheres.

(4) Purified standards are provided in the kit for the analyte quantitation and consist of known concentrations of purified analyte (unlabeled for sandwich or direct assay and element-labeled for competition assay) and enable calibration curves to be prepared. The standards should be free of high mass elements or chelators that would interfere with element analysis and are preferably lyophilized in a sterile buffered protein base with a preservative.

(5) Diluent (or dilution) buffers may also be provided for dilution of the purified element-tagged biologically active materials, element-tagged competition analyte, standards or the analyte. Diluent buffers are preferably: sterile, free of high mass elements or chelators, non-toxic, and designed to retain solubility, binding affinities, and native forms of element-tagged biologically active materials, element-tagged competition analyte, and the analyte to be analyzed. The buffers may comprise sterile proteinaceous buffers with preservatives and free from high mass elements or chelators. Diluent buffers for aptamers should be DNase and RNase free and may require DNase or RNase inhibitors to prevent aptamer degradation. Suggested dilution factors may also be included.

(6) The assay buffers are used to pre-treat the support prior to the assay. These buffers will serve to pre-wet, optimize the pH, chemically activate the supports to be used, or any combination of the above. Assay buffers are preferably: sterile, free of high mass elements or chelators, non-toxic, and designed to retain solubility, binding affinities, and native forms of element-tagged biologically active materials and element tagged competition analytes to be analyzed.

(7) The wash buffers are also included in the kit for washing excess unbound element-tagged reagent from the assay. These buffers are preferably: sterile, free of high mass elements or chelators, non-toxic, and designed to retain solubility, binding affinities, and native forms of element-tagged biologically active materials, element-tagged competition analytes, and the analyte to be analyzed.

(8) The elution buffer is used to suspend the element tag from the surfaces of microwell plates or beads to allow for introduction into an atomic mass or optical spectrometer and should be free of high mass elements with the exception of an elemental internal standard of known concentration. The tag does not necessarily have to be separated from the biologically active material or the beads. The elution buffer may preferably be an acid that allows complete solubility of the sample (tag, analyte, antigens, proteins, and aptamers) and separation from plate or bead support. Preferably the elution buffer is also spiked with an element or enriched isotope that has not been used as a tag. The spike will allow for monitoring of any instrumental drift. The elution buffer may not be required for microsphere assays, in which case, reacted microspheres may be suspended in wash buffer and introduced directly into the atomic mass or optical spectrometry.

(9) Instructions or protocols may also be included for conducting the assays according to the methods described in the invention.

Kits are provided for the second aspect of the invention for the determination of elemental species. Examples 11, 12 and 13 describe this aspect of the invention. The kits may include 1) a biologically active material (for example, an antibody or apatmer) specific to the elemental species, 2) buffers as described above and 3) instructions for carrying out the protocols as described herein.

Kits are also provided for the third aspect of the invention that involves direct labeling of the analyte. Examples 9 and 17 describe this aspect of the invention. The kits may include 1) a tag comprising a transition element, 2) reagents for tagging the analyte with a transition element as is known to those skilled in the art, 3) reagents for running a sample containing the tagged analyte on an electrophoresces gel, 4) buffers as described above and 5) instructions for carrying out the protocols as described herein.

In light of the present disclosure, those skilled in the art will readily appreciate other methods and applications of the methods of the present invention.

The examples below are non-limiting and are merely representative of various aspects and features of the present invention.

EXAMPLES

Example 1

NANOGOLD™ immunoassay

The following provides an example of the methods of the invention using the NANOGOLD-IgG™ (or NANOGOLD-Fab'™; Nanoprobes) immunoassay and its protocol. PBS buffer A is prepared as follows: 15 mM NaCl; 2 mM sodium phosphate, pH 7.4; 1% BSA (bovine serum albumin). All eppendorf tubes, micro-titer plates, and filters to be used subsequently are treated with PBS buffer A for 1 hour at room temperature to block non-specific binding. This treatment will reduce the non-specific interactions that occur between the plastic used and the analyte and NANOGOLD-IgG™. Alternatively low retention plastic products can be used (e.g. Axygen tubes). Following this a solution of the analyte (peptide, protein, etc.) in the concentration range of 1000 to 0.5 pg/µl in PBS buffer A is prepared. All dilutions are stored on ice. Subsequently, 100 µl of either analyte dilution or PBS buffer A (for controls) is pipetted into the individual wells of the micro-titer plate (or set of eppendorf tubes). The NANOGOLD-IgG™ is pre-filtered through 300 kDa (MICRCON™ or CENTRICON™) centrifugal filter devices. Dilutions of filtered NANOGOLD-IgG™ in PBS buffer A are prepared as follows: A 1:50 dilution is produced by adding 60 µl of NANOGOLD-IgG™ in 2940 µl PBS buffer A. A 1:500 dilution is then produced by adding 100 µl of 1:50 NANOGOLD-IgG™ to 900 µl of PBS buffer A. Depending on concentration range of analyte, 100 to 500 µl of 1:500 NANOGOLD-IgG™ is then added to the wells of the plate and then incubated for 1-2 hours at room temperature. The total amount of analyte- NANOGOLD-IgG™ mix is then pipetted into the sample reservoir (upper chamber) of a 300 kDa MICROCON™ centrifugal filter device (max volume 2 ml). This sample is centrifuged at 14,000 g for 15 minutes at room temperature. The assembly is removed from the centrifuge and the vial separated from sample reservoir. The sample reservoir is inverted in a new vial, and spun for 3 minutes at 1000 g to transfer the concentrate to a new vial. Finally, a fixed volume of the collected analyte- Nanogold-IgG™ antibody mixture is diluted to 1 ml with 10% HCl/1 ppbIr for stabilization. Ir provides an internal standard for ICP-MS quantitation and the acid solution is suitable for the elemental analysis. The linearity of the ICP-MS detector response as a function of the concentration of the analyte human IgG is shown in the results presented in FIG. 1.

Example 2

Immunoassay, Other than NANOGOLD-1 gG™ and Assay with aptamers

According to this example, an antibody is tagged with an element (eg. Eu, Ru, etc.) suitable for analysis by ICP-MS and is introduced into a sample containing an analyte which is an antigen of interest (e.g. human blood proteins). The element-tagged antibody reacts specifically to the target analyte. The resulting tagged analyte complex is separated from un-reacted antibody (as in Example 1, 3, 4, 5, 8, 9, or 10), and the tagged complex is analyzed by ICP-MS. Variations of this example include:

a) Tagging with multiple atoms to amplify the signal and thereby improving detectability.

b) As, a), except the tag contains several isotopes of the same element or different elements, preferably in a non-natural (unusual) distribution, so that the unique isotope distribution is a determinant of the targeted analyte. It is to be recognized that there are more than 80 naturally occurring elements) of which some 60 may have value in this application) having more than 250 stable isotopes. This allows construction of an enormous number of distinguishable tags. For example, there are 20 distinguishable 3-atom tags that may be constructed from only 4 different isotopes, and one million distinguishable 15-atom tags from 10 different isotopes, or 70-atom tags from 5 different isotopes.

c) As in a) and b), but incorporating different antibodies with specificity to different target molecules, to allow simultaneous determination of different target molecules. The number of simultaneous determinations is limited by the number of distinguishable tags in combination (which is fewer than the number of distinguishable tags in isolation as described above).

d) Using aptamers, Fab', Fab groups in place of antibodies. This is useful when the analyte that you are interested in binding or quantitating is too small or too toxic to have an antibody made that will bind efficiently to it.

Example 3

Protein A SEPHAROSE Immunoassay

The following provides an example of the methods of the invention using the Protein A SEPHAROSE CL-4B™ (Pharmacia) immunoassay and its protocol. Either NANOGOLD-Fab'™ or another element-labeled Fab' specific to the target analyte (or host species of the secondary antibody) may be used. There are three types of immunoassays that may be used:

a) Direct immunoassay, which would involve trapping the target protein of interest (protein X) by incubating Protein A SEPHAROSE CL-4B™ with an excess of antibody specific to the target analyte, washing off the un-reacted antibody, adding the analyte-containing sample, washing off the unbound components, and then exposing the PAS-antibody-protein X complexes to element-labeled, anti-X Fab'. This is also referred to as a sandwich assay.

b) Indirect immunoassay which would involve trapping the target protein of interest (protein X) by incubating Protein A SEPHAROSE CL-4B™ with an excess of primary antibody (e.g. polyclonal) specific to the target analyte, washing off the un-reacted primary antibody, adding the analyte-containing sample, washing off the unbound components, and then exposing the PAS-antibody-protein X complexes to a second antibody specific to protein X (e.g. a monoclonal antibody), washing off un-reacted secondary antibody, and then incubating the PAS-antibody-protein X-antibody complexes with an element-labeled, anti-secondary Fab'. Alternatively beads or micro-titer plates covalently bound to anti-protein X antibodies may be used. This is also referred to as an indirect sandwich assay because proteins are anchored to a surface using a capture molecule.

c) Competition immunoassay, which would involve trapping the target protein of interest (protein X) by incubating Protein A SEPHAROSE CL-4B™ with an excess of antibody specific to the target analyte, washing off the un-reacted antibody, adding the analyte-containing sample, washing off the unbound components, and then exposing the PAS-antibody-protein X complexes to a known amount of purified element-labeled protein X.

PBS buffer A is prepared as follows: 150 mM NaCl; 20 mM phosphate, pH 7.4; 1% BSA (bovine serum albumin). All eppendorf tubes, micro-titer plates, and filters, and slurry of Protein A SEPHAROSE CL-4B™ to be used subsequently are treated with PBS buffer A for 1 hour at room temperature to block non-specific binding. This treatment will reduce the non-specific interactions that occur between the plastic used and the analyte and NANOGOLD-Fab'™. Alternatively low retention plastic products can be used (e.g. Axygen tubes). Following this a solution of the analyte (peptide, protein, etc.) in the concentration range of 1000 to 0.5 pg/μl in PBS buffer A is prepared. All dilutions are stored on ice. Subsequently, 100 ul of either analyte or PBS buffer A (for controls) is pipetted into the individual wells of the micro-titer plate (or set of eppendorf tubes). To remove large unbound gold particles, the NANOGOLD-Fab'™ is pre-filtered through 300 KDa MICRCON™ (or CENTRICON™) centifugal filter devices. Dilutions of filtered NANOGOLD-Fab'™ in PBS buffer A are prepared as follows: A 1:50 dilution is produced by adding 60 μl of NANOGOLD-Fab'™ in 2940 μl PBS buffer A. A 1:500 dilution is then produced by adding 100 μl of 1:50 NANOGOLD-Fab'™ to 900 μl of PBS buffer A. Depending on concentration range of analyte, 100 to 500 μl of 1:500 NANOGOLD-Fab'™ is then added to the wells of the plate and then incubated for 1-2 hours at room temperature. The sample is centrifuged at 14,000 rpm for 2 minutes at room temperature. The beads are washed four times with PBS buffer A. In method b) the additional steps to include consist of incubating the beads (and attached analyte) with unlabeled primary antibody, washing off un-reacted monoclonal antibody, and then incubating the PAS-antibody-protein X-antibody complexes with an element-labeled, anti-X Fab'. Finally, a fixed volume of 10% HCl/1 ppbIr is added to each well. Ir provides an internal standard for ICP-MS quantitation and the acid solution is suitable for the elemental analysis.

Figure 2:
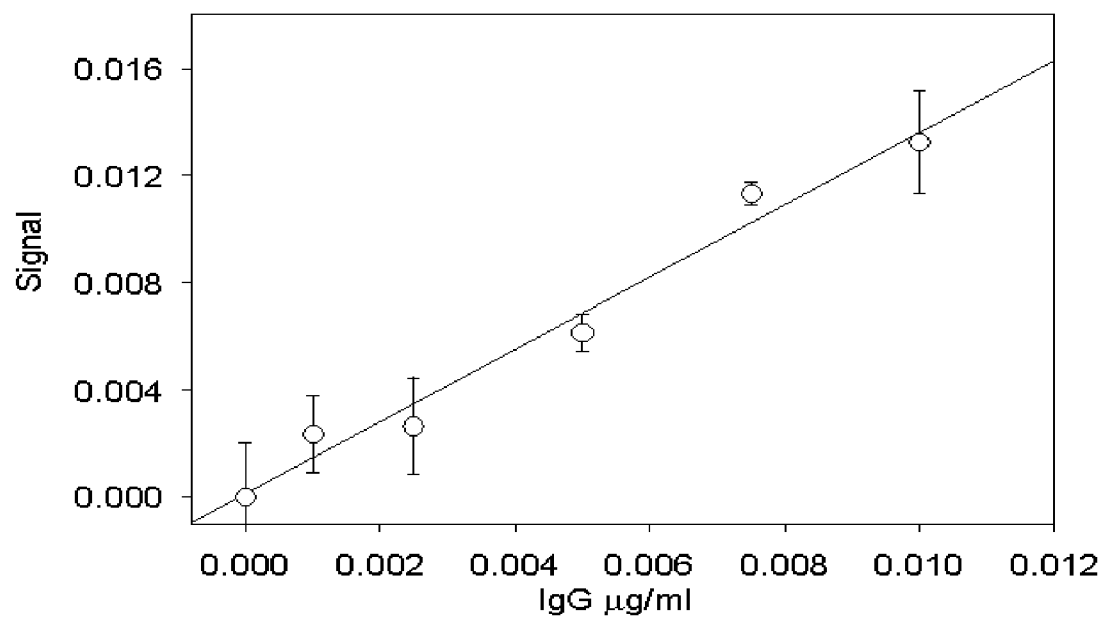
FIG. 2 is graph showing the results of an immunoassay with human IgG and Fab'-Au, over a low concentration range with detection and quantitation using ICP-MS.
Figure 3:
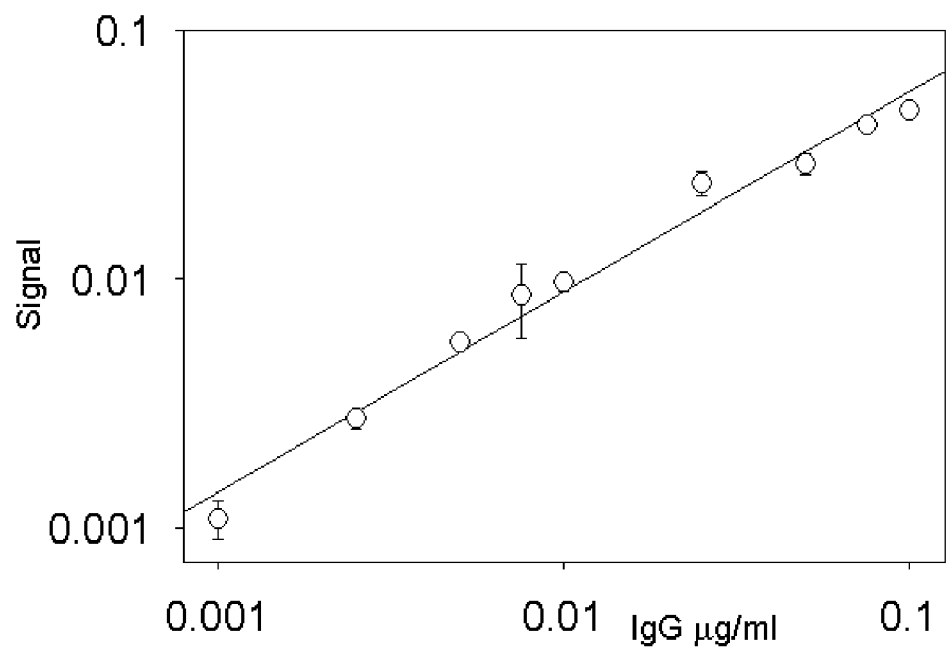
FIG. 3 is a graph showing the results of an immunoassay with human IgG and Fab'-Au, over a high concentration range with detection and quantitation using ICP-MS.

Experimental results obtained according to method a) are given in FIGS. 2 and 3, using human IgG as the analyte with F'ab-Au as the tagged antibody. FIG. 2 provides the calibration results over a relatively low concentration range, and FIG. 3 over a higher concentration range. Together, the data exhibit greater than 3 orders of magnitude of detector linearity with respect to the analyte concentration.

This Example also permits multiplexing to be analyzed and can be used to identify protein-protein interactions. In this method, cell lysate is collected and subjected to the method as above where an interaction is suspected between protein A and protein B. In this case the primary antibody would be specific to protein A and an element-labeled Fab' would be specific to protein B. Interactions with multiple other proteins (e.g. protein C and protein D) could be detected at the same time, providing that different elements were used to label anti-Fab' specific to protein C and anti-Fab' specific to protein D.

Example 4

DYNABEADS™ Immunoassay

The following method provides an example of the invention using the DYNABEADS™ (DYNAL) immunoassay and its protocol. This immunoassay is performed as in Example 3, using DYNABEADS™ in place of Protein A SEPHAROSE CL-4B™. Instead of centrifuging the sample, the sample is exposed to a magnetic device (DYNAL MPC™). This draws the beads to the bottom of the wells between and after each wash step. Again, 10% HCl/1 ppbIr is added to each well in the final step to provide an internal standard for ICP-MS quantitation and elemental analysis.

In the same manner as described for Example 3, multiplexing and protein-protein interactions can be identified using this method.

Example 5

Method for Detection and Quantification of Endogenous Proteins in Cultured Cells There are two methods by which the discrete changes in the levels of endogenous proteins in culture cells can be measured.
a) Direct immunoassay, in which an antibody specific to the protein of interest is required. This antibody is labeled with an element suitable for analysis by ICP-MS.
b) Indirect immunoassay, in which an antibody (primary antibody) specific to the protein of interest is required. In addition a secondary antibody specific to the primary antibody is labeled with an element suitable for analysis by ICP-MS.

A mono-layer of attached cultured cells is grown and treated with conditions of interest. The growth media is removed and the cells are washed with 1× PBS three times. PBS is then replaced with ice-cold methanol and the culture dishes are incubated at −20° C. for 5 minutes. The methanol is removed and the cells are allowed to dry completely. An assay buffer (e.g. 10% horse serum, 1% BSA, 0.05% TWEEN-20, 1× PBS) is added to the culture dishes and the dishes are incubated for 1-2 hours at room temperature. In method a) an antibody specific to the protein of interest is labeled with an element, diluted in dilution buffer and added to the culture dishes. The cells are exposed to the antibody mix for 2 hours at room temperature (or 37° C.). The trademark TWEEN-20 refers to a surfactant, namely p lyoxyethylene monolaureat, n ca.20. The un-reacted primary antibody is washed away with wash assay buffer. During this time, the element-tagged antibody binds the target protein. In method b) the antibody specific to the protein of interest is not labeled and is diluted in dilution buffer and added to the culture dishes. The cells are exposed to the antibody mix for 2 hours at room temperature (or 37° C.). In the next step, the un-reacted primary antibody is washed away with wash buffer. In method b) the element-labeled secondary antibody is diluted in assay buffer and applied to the cells. The dishes are incubated for 1-2 hours at room temperature. The un-reacted secondary antibody is then washed away with wash buffer. Finally, in both methods, an acid solution (e.g. concentrated HCl) is added, to release and dissolve the tagging element. The dissolved element in acid is diluted with 10% HCl/1 ppb Ir to provide an internal standard. The acid solution containing the tagging element is then analyzed by ICP-MS to quantify the protein of interest.

Figure 4:
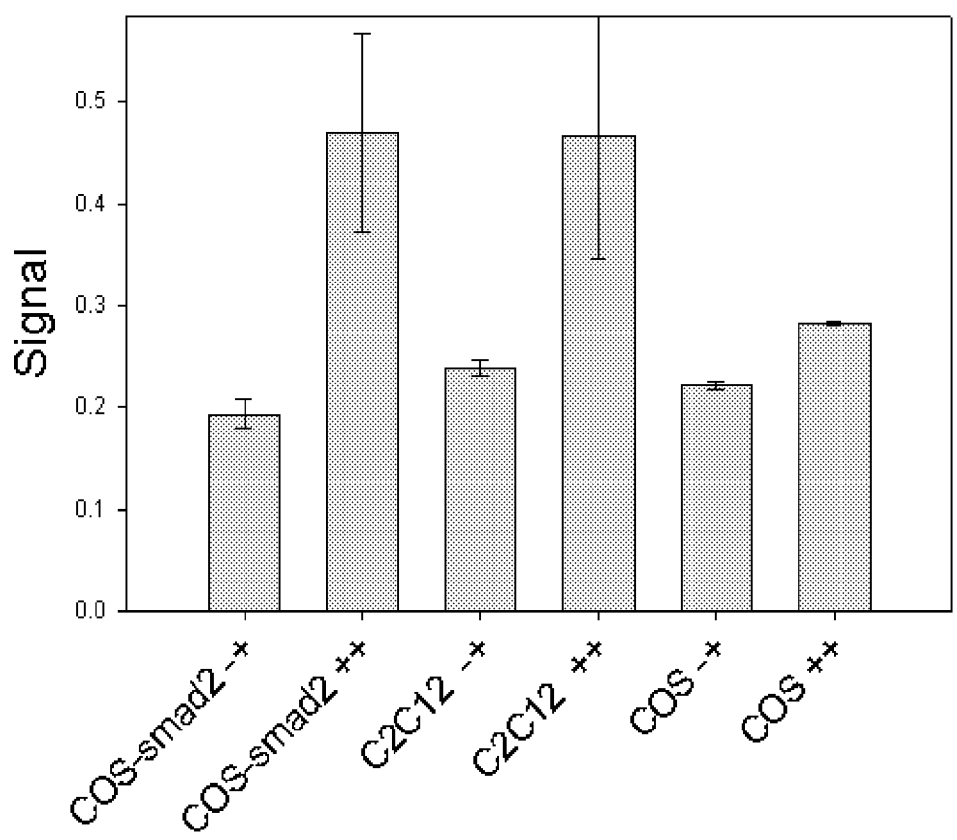
FIG. 4 is a bar graph showing the results of measuring endogenous protein in cultured cells with detection and quantitation using ICP-MS.

Experimental data obtained according to method b) is shown in FIG. 4. This data examines the sensitivity of this immunoassay, by comparing the relative amounts of Smad2 in three different cell cultures; COS (Bars 5 and 6), COS transfected with pCMV5B-Smad2 (COS-smad2) (Bars 1 and 2), and C2C12 cells (Bars 3 and 4). COS cells are known to have undetectable levels of Smad2 protein (using Western blot analysis). Conversely, Smad2 is detectable in C2C12 cell lysate and in COS cells that have been transfected with pCMV5B-Smad2. These cell cultures are prepared in 60 mm dishes, fixed with methanol, blocked with TBST buffer and then incubated in either the presence (Bars 2, 4, and 6) or absence (Bars 1, 3, and 5) of polyclonal anti-Smad2 antibody (Upstate Biotech). The cells are then incubated with a gold-tagged anti-rabbit antibody (Nanoprobes), dissolved in concentrated HCl, diluted 2 fold in 10% HCl/1 ppb Ir and analyzed using the ICP-MS. Each bar is an average of triplicate samples. Bars 1, 3, and 5 reflect negative control cultures not treated with primary antibody (∓). Cultures treated with both primary and secondary antibodies (++) show that in the two cell cultures that express Smad2, a substantial increment in the signal over the (+−) results indicates the presence of the Smad2 protein. The third culture, COS, which is not expected to express Smad2, shows a signal for the (++) case that is roughly comparable to that of the blank (+−).

Example 6

Method for Determination Efficiency of Cell Transfection

The effectiveness of the cell culture transfection is determined by first modifying cells to transduce a tail (e.g. FLAG™). This protocol is useful when antibodies against the analyte of interest are not available. In this case, the expression of a recombinant analyte containing recognizable tails such as Flag, HIS (histidine) or GST (glutathione S-transferase) are particularly useful as antibodies against these moieties are readily available. As in Example 5, there are two methods by which the analyte of interest can be detected (directly and indirectly).
a) Direct immunoassay, in which an antibody specific to the tail is required. This antibody is labeled with an element suitable for analysis by ICP-MS.
b) Indirect immunoassay, in which an antibody (primary antibody) specific to the tail is required. In addition a secondary antibody specific to the primary antibody is labeled with an element suitable for analysis by ICP-MS.

Between 1-3 days after transfection of the cells, the growth media (typically 10% FBS, depending on cell-type) is removed and the mono-layer of attached cells are washed with 1× PBS three times. PBS is replaced with ice-cold methanol and the culture dishes are incubated at −20° C. for 5 minutes. The methanol is removed and the cells are allowed to dry out completely. An assay buffer (e.g. 10% horse serum, 1% BSA, 0.05% TWEEN-20, 1× PBS) is added to the culture dishes and the dishes are incubated for 1-2 hours at room temperature. In method a) an antibody specific to the tail is produced and labeled with an element that is suitable for analyzing with the ICP-MS. The antibody is diluted in dilution buffer and added to the culture dishes. The cells are exposed to the antibody mix for 2 hours at room temperature (or 37° C.). During this time, the element-tagged antibody binds the target protein through its tail. In method b) the antibody specific to the protein of interest is not labeled. In both cases, the un-reacted primary antibody is washed away with wash buffer. Then, in method b) the element-labeled secondary antibody is diluted in dilution buffer and applied to the cells. The dishes are incubated for 1-2 hours at room temperature. The un-reacted secondary antibody is washed away with wash buffer. Finally, in both methods, an acid solution (e.g. concentrated HCl) is added, to release and dissolve the tagging element. The dissolved element in acid is diluted with 10% HCl/1 ppb Ir to provide an internal standard. The acid solution containing the tagging element is analyzed by ICP-MS to quantify the efficiency of the transfection. Culture dishes containing non-transfected cells cultured at the same time can be used as a negative control An alternate variation of this Example involves using a 6× HIS- TAGGED CONSTRUCT™ (Invitrogen), where there is no need for analyte-specific antibodies. Cells transfected with 6× HIS-TAGGED CONSTRUCTS are fixed with methanol, blocked with the assay buffer and incubated for 2 hours with a solution containing nickel (e.g. Ni—NTA™; Qiagen). The cells are washed to remove free nickel, degraded in acid degraded, and analyzed using ICP-MS for nickel content.

An alternate variation of this Example involves using a 6×HIS-tagged construct™ (Invitrogen), where there is no need for analyte-specific antibodies. Cells transfected with 6×HIS-tagged constructs are fixed with methanol, blocked with the assay buffer and incubated for 2 hours with a solution containing nickel (e.g. Ni-NTA™; Qiagen). The cells are washed to remove free nickel, degraded in acid degraded, and analyzed using ICP-MS for nickel content.

Example 7

Reporter Assay

In the study of transcription factors, it is necessary to quantitate the levels of transcription. There are two methods by which discrete changes in the levels of transcription activity on a specific promoter (or enhancer elements) can be measured. Cultured cells are transfected with expression plasmids of interest along with equal amounts of plasmid containing the promoter of interest linked to a reporter gene (e.g. GFP). As in Example 5 there are two methods by which the analyte of interest can be detected (directly and indirectly).
  a) Direct immunoassay, in which an antibody specific to the reporter is required. This antibody is labeled with an element suitable for analysis by ICP-MS.
  b) Indirect immunoassay, in which an antibody (primary antibody) specific to the reporter is required. In addition a secondary antibody specific to the primary antibody is labeled with an element suitable for analysis by ICP-MS.

Cultured cells are grown and transfected with conditions of interest. Upon analysis, the growth media is removed and the cells are washed with 1× PBS three times. PBS is replaced with ice-cold methanol and the culture dishes are incubated at −20° C. for 5 minutes. The methanol is removed and the cells are allowed to dry out completely. An assay buffer (e.g. 10% horse serum, 1% BSA, 0.05% TWEEN-20, 1× PBS) is added to the culture dishes and the dishes are incubated for 1-2 hours at room temperature. In method a) an antibody specific to the reporter is labeled with an element, diluted in dilution buffer and added to the culture dishes. The cells are exposed to the antibody mix for 2 hours at room temperature (or 37° C.). During this time, the element-tagged antibody will bind the reporter. In method b) the antibody specific to the reporter is not labeled. In both cases, the un-reacted antibody is then washed away with wash buffer. In method b) the element-labeled secondary antibody is diluted in dilution buffer and applied to the cells. The dishes are incubated for 1-2 hours at room temperature. The un-reacted secondary antibody is then washed away with wash buffer. Finally, in both methods, an acid solution (e.g. concentrated HCl) is added, to release and dissolve the tagging element. The dissolved element in acid is diluted with 10% HCl/1 ppb Ir to provide an internal standard. The acid solution containing the tagging element is analyzed by ICP-MS to quantify the protein of interest.

Example 8

Detection of Proteins After Electrophoresis Using Tagged Antibodies

A sample of proteins is diluted in 2× SDS sample buffer (1% SDS, 2% glycerol, 1000 mM Tris, pH6.8, 5% β-mercaptoethanol, 1% DTT, 1% PMSF, 0.2% leupeptin, 0.2% pepstatin) and exposed to electrophoresis on a 2-D or polyacrylamide gel (SDS-PAGE or N-PAGE) to separate the proteins. The proteins from the gel are transferred to nitrocellulose using a semi-dry electrophoretic transfer apparatus (or equivalent). The nitrocellulose is blocked for 1 hour at room temperature using a assay buffer (e.g. 5% milk in 1× PBS). An element-tagged antibody that recognizes the target protein is added to assay buffer and the nitrocellulose blot is exposed to the antibody-containing buffer for 2 hours at room temperature. Alternatively an un-labeled primary antibody that recognizes the target protein is used to bind the target protein, followed by washes with wash buffer, and then probing with a secondary anti-primary antibody that is labeled with an element. The nitrocellulose blot is washed three times with wash buffer (0.2% NP40 in 1× PBS). The protein in question is analyzed and quantified by laser ablation.

Example 9

Detections of Proteins After Modification with 6× HIS-TAG™ (Invitrogen) and Separation by Electrophoresis This Example is similar to Example 8; however, the proteins in the sample are modified prior to electrophoresis so that they have an affinity for an element (e.g. the 6× HIS modification yields affinity to Nickel). The gel or blotting paper containing the separated proteins is washed with a solution containing an element (e.g. Ni) that is bound by the protein modification. The gel or blotting paper is analyzed by laser ablation (or direct excisions and elutions) and ICP-MS.

Example 10

Size Exclusion Gel Filtration Immunoassay

In this example, ICP-MS is used to detect the presence of a specific analyte. Accordingly, an antibody is tagged with an element (eg. Au, Eu, Ru, etc.) and is introduced into a sample containing the analyte of interest. The elemental-tagged antibody reacts specifically to the target analyte. The resulting tagged analyte complex is separated from un-reacted antibody using gel filtration (e.g. HIPREP SEPHACRYL™;

Pharmacia) in a running buffer containing 1 ppbIr. The eluate is collected in 0.5 ml increments into a 96 well plate, diluted in acid, and analyzed by ICP-MS.

Figure 5:
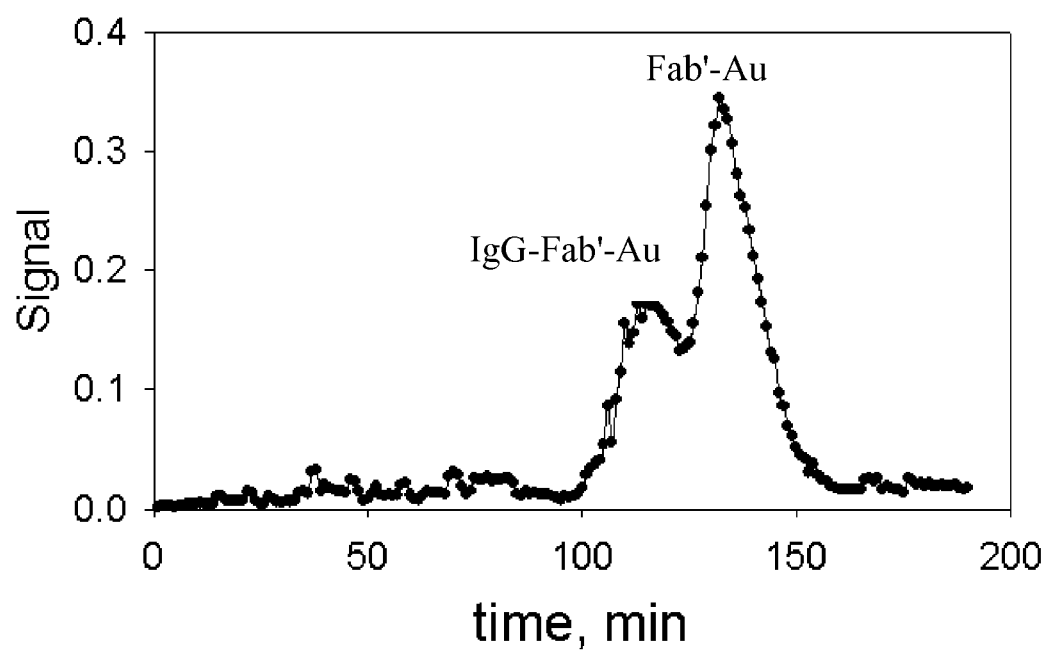
FIG. 5 is a graph showing the detection and quantitation of a specific analyte by ICP-MS.

Experimental results obtained according to this method for IgG analyte using Fab'-Au antibody are shown in FIG. 5. In this experiment an IgG analyte is incubated with an excess of Fab'-Au. The sample is run through a sephacryl S-200 column at a flow rate of 0.5 ml/min, using a running buffer of 0.15M NaCl, 0.02M phosphate, pH 7.4, 1 ppb Ir. The figure provides the detector response as a function of elution time (eluate number). The first peak observed (the heavier molecular weight) corresponds to the reacted complex, having an expected molecular weight of about 235 kDa. The second peak corresponds to the unreacted tagged antibody having an expected molecular weight of about 85 kDa.

Example 11

Detection and Quantitation of Elemental Species

In this example, ICP mass spectrometry is used to measure a quantity of metal identified by an antibody which is specific for a given molecular form or species of a given metal. A solution containing the analyte is then incubated with an antibody, which is specific for the molecular form of the given metal. This solution is treated to separate antibody-metal species complexes from un-reacted antibody and the remainder of components in the sample, although it is important only that species of the given metal other than the species of interest be removed from the sample.

Preferably, the antibody exhibits little or no ability to bind to species other than the species of interest and exhibits a tight and specific binding of the metal species which is to be measured. Preferably, this binding affinity shows an equilibrium dissociation constant ($K_D$) on the order of $10^{-9}$ to $10^{-8}$M. The antibody used in such assays also is able to resist interference from other components contained in the sample, which is being assayed. The solution containing the antibody-metalspecies complexes is subject to standard ICP-MS/OES analysis. This approach removes the necessity for a chromatographic pre-separation and consequently improves the sample integrity. It also allows for simultaneous measurement of several elemental species, the method being limited only by the number of antibodies introduced to the sample.

Example 12

Detection and Quantitation of Elemental Species Using Tagged Antibodies

According to this Example, as in Example 11, antibodies specific for metal-species are raised according to methods well known to those skilled in the art. The difference in this Example is the antibody is tagged with multiple atoms of a given tagging isotope, or a stoichiometric mixture of isotopic tags. This has two potential advantages. First, in the event that the target metal element is subject to interference in analysis through typical ICP-based interferences (for example argide ion isobaric interferences) tagging the antibody with a normally non-interfered tag allows for interference-free determination, resulting in improved detectablity. Secondly, specific tags for various species of the same target element allows simultaneous measurement of various species (which would not be provided if the elemental tag were the innate target element itself, since the presence of that element in the spectrum would indicate only that one or more of the target species is present). A further advantage according to this approach is that tagging with multiple atoms of the same isotope allows for signal amplification proportional to the number of atoms of the same tagging isotope.

Example 13

Simultaneous Detection of Numerous Elemental Species in a Sample Using Tagged or Untagged Antibodies According to this example, as in Example 11 and 12, antibodies specific for metalspecies are raised according to methods well known to those skilled in the art. The difference in this Example is that two or more antibodies specific to different elemental species are incorporated, to allow for the simultaneous determination of different speciations of the same or different elements (where each element is differentially tagged).

Example 14

Immunoassay to Detect Bovine Spongiform Encephalopathy (BSE) in Animal Products

The methods of Examples 1, 2, 3, 4, 5, 8, and/or 10 are employed to detect BSE in animal products. There are several monoclonal antibodies (15B3, Korth et al., 1997; KG9, Laffling et al., 2001; Bio-Rad Laboratories) that have been produced that target the prion protein PrP thought to be the infectious component responsible for the illness. Monoclonal antibodies specific to PrP are labeled with an element (eg. Au, Eu, Ru, etc.) and used in immunoassays described in either Example 1, 2, 3, 4, 5, 8, and/or 10. Similar products known to be free of BSE would be used as a negative control. In a similar manner other diseases detected for by antibody can be screened for (e.g. HIV, HTLV, Rabies, etc.).

Example 15

Immunoassay to Detect Ischemic Markers in Patients Believed to have Suffered a Heart Attack The methods of Examples 1, 2, 3, 4, 5, 8, and/or 10 are employed to simultaneously detect multiple ischemic markers in human samples. Candidate markers include: CK-MB, myoglobin, Troponin I, hsp70, BCL2, Bax, IGF, TNFα, angiostatin II.

Example 16

Method for Drug Discovery

In order to aid in drug discovery, animal cells or animal receptors are placed in multi-well plates. The molecule of interest is added (i.e. potential drug), as well as element-tagged antibody (or element tagged ligand) that recognizes the receptor. The potential drug is in competition with the antibody for adhesion to the receptor. Unbound antibody is washed away, and the amount of bound antibody is determined by ICP-MS. This is inversely proportional to the effectiveness of the potential drug to recognize the receptor. If each well is provided with differently labeled antibodies, then by combining the contents of the wells, one can simultaneously assess the effectiveness of various drugs, or drug compositions by deconvoluting the resultant data. Likewise, differently labeled antibodies for the same analyte can be produced and placed in corresponding wells of different plate (i.e. 10 differently labeled version of the antibody, each one placed in well 1, 1 in 10 plates). The plate contents are combined, the reacted antibodies are separated and analyzed simultaneously, with de-convolution to determine the analyte concentration in the corresponding well of each plate.

Example 17

Detection of Tagged Proteins Using 2D Gel and Mass Spectrometry

In this example, the ICP-DRC-MS technique is used in conjunction with the laser ablation of polyacrylamide gels containing proteins tagged by iron. It is well known that $ArN^+$ and $ArO^+$ interfere with $^{54}Fe^+$ and $^{56}Fe^+$, respectively. To facilitate the method described in Example 9, it is essential to remove isobaric poly-atomic interferences from the iron isotopes. For example, the ratio of the mass spectrometric signals at m/z=54:m/z=56 (where m/z indicates the mass-to-charge ratio of the ion) measured directly by ablation of the polyacrylamide gel containing a protein band tagged by iron was found to be 1.14 (whereas the expected value, based on the natural abundance of the iron isotopes, is 0.063). Utilizing ammonia as a reaction gas in the DRC environment, it is possible to eliminate $ArN^+$ and $ArO^+$ interferences by charge transfer reaction. This approach yielded the m/z=54:m/z=56 ratio that approximated the expected $^{54}Fe^+/^{56}Fe^+$ isotope ratio, by which agreement the determination of the tag iron can be confirmed. In addition, the precision of this measurement is significantly improved due to partial temporal equilibration of ions in the gaseous media of the reaction cell (see Bandura, D. R., et al. 2000).

Example 18

Detection of a Protein Using an Element-Tagged Aptamer

In this example, an element-tagged aptamer is used to detect and measure a protein in a sample.

Aptamers that bind a protein can be prepared using techniques known in the art such as those described in Ellington A D and Szostak J W. (1990); Turek C and Gold L (1990); Robertson D L and Joyce G F (1990); Gold, L, Polisky, B, Uhlenbeck, O, and Yarus, M (1995); Szostak, J W (1995).

Aptamers may be labeled as is known to those skilled in the art.

A solution of the protein in the concentration range of 1000 to 0.5 pg/μl in PBS buffer A is prepared. All dilutions are stored on ice. Subsequently, 100 μl of either protein dilution or PBS Buffer A (for controls) is pipetted into individual wells of a micro-titre plate (or eppendorf tubes). The element-tagged aptamer is pre-filtered through 300 kDa centrifugal filter devices, such as MICRON™ or CENTRICON™). Serial dilutions of the tagged aptamer are prepared as is known to those skilled in the art. Depending on the concentration range of the protein, 100 to 500 μl of the tagged aptamer is added to the wells or tubes and incubated for 1-2 hours at room temperature. Following incubation, the combined sample is filtered in a centrifugal filter device as described above, for 15 minutes at 14,000 g at room temperature. The sample reservoir is inverted in a new vial and spun for 3 minutes at 1000 g to transfer the concentrate to a new vial. A fixed volume of the collected protein-aptamer mixture is diluted to 1 ml with 10% HCl/1 ppbIr for stabilization and analyzed in a mass spectrometer.

Example 19

Preparation of Kits Comprising Reagents for Cytokine Analysis

In this example, assay kits are prepared for the purpose of detecting and measuring either a single cytokine or multiple cytokines simultaneously using an atomic mass or optical spectrometer. The kits may comprise reagents for (a) direct affinity assays, (2) sandwich affinity assays, (3) competitive affinity assays, or any other assays that utilize element-tagged biologically active materials or element-tagged analytes that are detected by an atomic mass or optical spectrometer. The element-tagged affinity assays involve three basic steps. First the target cytokine(s) from a sample (for example, EDTA-plasma) is bound to supports such as microwell plates, beads or microspheres. A solid support is not required if separation of reaction products (ie. bound tagged biologically active material from unbound tagged biologically active material) is achieved by chromatography (eg. size exclusion gel filtration or centrifugal filtration) instead of by washing. This may be done using affinity, ionic or covalent bonding. Second, the target cytokine(s) is either complexed with an element-tagged biologically active material (for example, an element-tagged aptamer or antibody) or in the case of competitive assay, element-tagged cytokines are added to bind the remaining surface attachment sites. Third, after washing, the amount of element tag that has been complexed is measured using an atomic mass or optical spectrometer.

1) Preparation of the element-tagged biologically active materials (for example, antibodies, aptamers) and element-tagged competition analytes (for example, element-tagged cytokines) for the kit. For direct or sandwich affinity assays, detection of biologically active materials) (for example, antibodies or aptamers) are raised against the cytokines of interest to be measured. The cytokines of interest may include, Human IFNγ, Human TNFα, Human IL-1β, Human IL-4, Human IL-5, Human IL-6, Human IL-8, and Human IL-13. These detection antibodies or aptamers are tagged with element tags. Preferably, they are tagged in a covalent manner. For competitive assays, competition analytes (for example, cytokines) are tagged with elemental tags. Preferably, they are tagged in a covalent manner. It is desirable to tag each pool of antibody, aptamer, or cytokine with different elemental or isotopically enriched tags. For example, anti-Human IFNγ-$Sm^{152}$, anti-Human TNFα-$Eu^{151}$, anti-Human IL-1β-$Dy^{164}$, anti-Human IL-4-$Eu^{153}$, anti-Human IL-5-$Tb^{159}$, anti-Human IL-6-$Pr^{141}$, anti-Human IL-8-$Sm^{154}$, and anti-Human IL-13-$Gd^{158}$ are prepared. To avoid tagging the active sites of aptamers due to their small size, it may be necessary to construct pre-labelled aptamer libraries, so that element-tagged aptamers are selected and produced based on their affinities to the respective cytokines. Optionally, if element-tags are not found to interfere with affinities, it may be easier to tag after the selection process. Both options are available. Alternatively, the kits may simply include a tag comprising a transition element with instructions for tagging the biologically active material or competition analyte. Preparation of tags comprising transition elements are known to those skilled in the art.

2) Purification of element-tagged biologically active materials (for example, antibody, aptamer) or element tagged competition analytes (for example, cytokines). The element-tagged antibody, aptamer or cytokine is purified preferably using size exclusion chromatography, affinity chromatography, filtration, or dialysis.

3) Several supports (for example, columns, gels, plates, microwells and beads) have been designed for anchoring molecules (for example, analytes, aptamers or antibodies) through for example, the following mechanisms which include but are not limited to: (a) hydrophobic interactions, (b) hydrophilic interactions, (c) covalent reactions with amine and sulfhydryl groups, (d) avidin interactions with biotynlated antibodies, (e) Fc (crystallizable fragment of an antibody) affinities for Protein A or Protein G, or (f) through affinities for nickel or glutathione. Some examples of plates used for antibody attachment are NUNC MAXISORP™, PIERCE MALEIC ANHYDRIDE™, PALL™ nitrocellulose and PVDF™ filter plates. Aptamer attachment may be achieved through several different methods, which includes but is not limited to: UV irradiation, covalent chemical bonds, or baking to glass, plastic, or membrane surface. Plates available include: NUNC COVALINK™ which use secondary amino groups to covalently bind 5'carboxyl group of DNA or RNA; and NUNC COVALINK™ which covalently bind 5' phosphorylated DNA. Various filter-plates (NUNC™, PALL™) are available which are convenient for preparing 96 well bead immunoassays simultaneously. Such filter-plates can be used in conjunction with vacuum or centrifuge and preferably have a pore size $1/10^{th}$ of the size of the beads being used. Other options of bead containment are available and obvious to those skilled in the art and can be used to substitute filter-plates in all instances.

4) Coating of the microwell plates or beads with capture anti-cytokine antibodies or aptamers. This can be done for the sandwich affinity assays and the competitive affinity assays. In the sandwich assay, preferably a matched pair of antibodies or a matched pair of aptamers for each of the cytokines that are to be quantitated is designed. A matched pair of antibodies is two antibodies that recognize distinct epitopes on the cytokine so that a cytokine may be bound with high affinity to both antibodies simultaneously. The antibodies may be monoclonal antibodies or polyclonal antibodies. A matched pair of aptamers is similar, in that two aptamers are developed towards distinct epitopes on the cytokine of interest so that the cytokine is bound with high affinity to both aptamers simultaneously. In a sandwich assay, one of the matched pair of antibodies or aptamers is coated on the microwell plates or beads and serves to capture the target cytokine in the sample anchoring it to the surface. The second antibody or aptamer functions as a detection agent and is labelled with an elemental tag. The coating of microwell plates for multiple cytokine detection may be done by a) pipetting a mixture of the capture antibodies or aptamers into each well or b) by spotting different antibodies or aptamers separately using different tips (e.g. robotic). The advantage of a spotting format is that the different capture antibodies or aptamers are kept separate and many different custom plates can be produced for analyzing different combinations of cytokines such that production is easily designed by robotic application.

5) In sandwich assays and competition assays, after coating the solid supports with capture molecules, for example antibodies or aptamers to prevent non-specific binding, it may be necessary to passivate or treat the microwell plates or beads and filter-plate using a assay buffer prior to being used in the kit protocol. The assay buffer may contain sterile proteinaceous buffer (e.g. 1% BSA in 1× PBS with preservatives).

6) Components of Element-tagged Direct Affinity Assay kit for the simultaneous detection and quantitation of multiple cytokines. The kits may contain all or some of the following components: 1) tags comprising transition elements, 2) element-tagged biologically active materials (for example, antibodies or aptamers), 3) cytokine binding solid supports, for example microwell plate(s) or beads and filter-plate(s), 4) standard cytokines (which will be comparable to the National Institute for Biological Standards and Control (NIBSC) standards), 5) diluent buffers for re-suspending standard cytokines and element-tagged reagents, 6) wash buffers, 7) elution buffers and 8) assay buffers (optional for pre-treating plates), 9) instructions and protocols for direct affinity assay for the simultaneous detection and quantitation multiple analytes.

7) Components of Element-tagged Sandwich Affinity Assay kit for the simultaneous detection and quantitation of multiple cytokines. The kits may contain all or some of the following components: 1)tags comprising transition elements, 2) element-tagged biologically active materials (for example, antibodies or aptamers), 3) pre-coated (with capture antibodies or aptamers) and pre-treated (with assay buffer) solid supports, for example microwell plate(s) or beads and filter-plate(s), 4) standard cytokines (which will be comparable to NIBSC standards), 5) diluent buffers for re-suspending standard cytokines and element-tagged reagents, 6) wash buffers, 7) elution buffers, and 8) assay buffers (optional for pre-treating plates), 9) instructions and protocols for sandwich affinity assay for the simultaneous detection and quantitation multiple analytes.

8) Components of Element-tagged Competitive Affinity Assay kit for the simultaneous detection and quantitation of multiple cytokines. The kits may contain all or some of the following components: 1) tags comprising transition elements; 2) element-tagged competition analytes (for example, cytokines), 3) pre-coated (with capture molecules, for example antibodies, aptamers or other analyte binding material eg. maleic anhydride groups or cytokine receptors) and pre-treated (with assay buffer) solid supports, for example microwell plate(s) or beads and filter-plate(s), 4) standard cytokines (which will be comparable to NIBSC standards), 5) diluent buffers for re-suspending standard cytokines and element-tagged reagents, 6) wash buffers, 7) elution buffers and 8) assay buffers (optional for pre-treating plates). 9) Protocols and instructions for the competitive affinity assay. Optionally, the solid supports can bind the analyte and competition analyte directly.

The kits may also include instructions or protocols for carrying out the assays. The following are some sample protocols:

9) Protocol for Element tagged Direct Affinity Assay kit for the simultaneous detection and quantitation of multiple cytokines.

a.) Prepare purified standard cytokines (which will be comparable to NIBSC standards) by adding a prescribed volume of standard cytokine diluent buffer (e.g. 1% BSA in 1×PBS) into each vial, allowing to dissolve for 5 minutes at room temperature, and inverting several times. Prepare serial dilutions (e.g. 1000 pg/ml, 500 pg/ml, 250 pg/ml, 125 pg/ml, 62.5 pg/ml, 31.2 pg/ml, 15.6 pg/ml, 7.8 pg/ml, 3.9 pg/ml, and 0 pg/ml).

b.) Prepare the sample containing cytokines of interest (eg. patient EDTA-plasma samples) by thawing, mixing and filtering if necessary.

c.) If beads are being used, beads must be suspended and diluted accordingly. Aliquote 100 μl of beads into each microwell of filter plate.

d.) Pipette an aliquot (eg. 100 μl) of either sample or serially diluted standard into each well (in duplicate or triplicate as desired). Shake on orbital shaker at room temperature for 1-2 hrs.

e.) Aspirate (or with beads and filter-plate use centrifuge or vacuum) and wash 3 times with 400 μl of wash buffer (e.g. 1% BSA in 1× PBS).

f.) Add an aliquote (eg. 100 μl) of element-tagged biologically active materials (for example, antibodies or aptamers) at appropriate dilution (in detection diluent buffer; e.g. 1% BSA in 1× PBS). Shake on orbital shaker at room temperature for 1-2 hrs.

g.) Aspirate (or with beads and filter-plate use centrifuge or vacuum) and wash 3 times with 400 μl of wash buffer (e.g. 1% BSA in 1× PBS).

h.) Aspirate (or with beads and filter-plate use centrifuge or vacuum) plate.

i.) Add 50-100 μl elution buffer containing an acid solution with elemental spike, preferably an element that is soluble in the acid and close to the same atomic mass as the elements to be measured (e.g. 3% HCl, 1 ppb Pr). Shake on orbital shaker at room temperature for 5-10 minutes.

j.) Measure and quantitate elements of interest using atomic mass or optical spectrometer, preferably ICP-MS.

10) Protocol for Element tagged Sandwich Affinity Assay kit for the simultaneous detection and quantitation of multiple cytokines.

a.) Prepare purified standard cytokines (which will be comparable to NIBSC standards) by adding a prescribed volume of standard cytokine diluent buffer (e.g. 1% BSA in 1× PBS) into each vial, allowing to dissolve for 5 minutes at room temperature, and inverting several times. Prepare serial dilutions (e.g. 1000 pg/ml, 500 pg/ml, 250 pg/ml, 125 pg/ml, 62.5 pg/ml, 31.2 pg/ml, 15.6 pg/ml, 7.8 pg/ml, 3.9 pg/ml, and 0 pg/ml).

b.) Prepare the sample containing cytokines of interest (eg. patient EDTA-plasma samples) by thawing, mixing and filtering if necessary.

c.) If beads are being used, beads must be suspended and diluted accordingly. Aliquote 100 μl of beads into each microwell of filter plate.

d.) Pre-treat microwell plate or beads and filter-plate with 400 μl of assay buffer (e.g. 1% BSA in 1× PBS) per well. Shake on orbital shaker at room temperature for 1-2 hrs. (optional, may not be necessary)

e.) Pipette an aliquot (eg. 100 μl) of either sample or serially diluted standard into each well (in duplicate or triplicate as desired). Shake on orbital shaker at room temperature for 1-2 hrs.

f.) Aspirate (or with beads and filter-plate use centrifuge or vacuum) and wash 3 times with 400 μl of wash buffer (e.g. 1% BSA in 1× PBS).

g.) Add an aliquote (eg. 100 μl) of element-tagged biologically active materials (antibodies or aptamers) at appropriate dilution (in diluent buffer; e.g. 1% BSA in 1× PBS). Shake on orbital shaker at room temperature for 1-2 hrs.

h.) Aspirate (or with beads and filter-plate use centrifuge or vacuum) and wash 3 times with 400 μl of wash buffer (e.g. 1% BSA in 1× PBS).

i.) Aspirate (or with beads and filter-plate use centrifuge or vacuum) plate.

j.) Add 50-100 μl elution buffer containing an acid solution with elemental spike, preferably an element that is soluble in the acid and close to the same atomic mass as the elements to be measured (e.g. 3% HCl, 1 ppb Pr). Shake on orbital shaker at room temperature for 5-10 minutes.

k.) Measure and quantitate elements of interest using atomic mass or optical spectrometer.

11) Protocol for Element tagged Competitive Affinity Assay kit for the simultaneous detection and quantitation of multiple cytokines.

a.) Prepare purified standard cytokines (which will be comparable to NIBSC standards) by adding a prescribed volume of standard cytokine diluent buffer (e.g. 1% BSA in 1× PBS) into each vial, allowing to dissolve for 5 minutes at room temperature, and inverting several times. Prepare serial dilutions (e.g. 1000 pg/ml, 500 pg/ml, 250 pg/ml, 125 pg/ml, 62.5 pg/ml, 31.2 pg/ml, 15.6 pg/ml, 7.8 pg/ml, 3.9 pg/ml, and 0 pg/ml).

b.) Prepare the sample containing cytokines of interest (eg. patient EDTA-plasma samples) by thawing, mixing and filtering if necessary.

c.) If beads are being used, beads must be suspended and diluted accordingly. Aliquote 100 μl of beads into each microwell of filter plate.

d.) Pre-treat microwell plate or beads and filter-plate with 400 μl of assay buffer (e.g. 1% BSA in 1× PBS) per well. Optionally, shake on orbital shaker at room temperature for 1-2 hrs.

e.) Pipette an aliquot (eg. 100 μl) of either sample or serially diluted standard into each well (in duplicate or triplicate as desired). Shake on orbital shaker at room temperature for 1-2 hrs.

f.) Aspirate (or with beads and filter-plate use centrifuge or vacuum) and wash 3 times with 400 μl of wash buffer (e.g. 1% BSA in 1× PBS).

g.) Add an aliquote (eg. 100 μl) of element-tagged competition analyte (for example, cytokines) at appropriate dilution (in diluent buffer; e.g. 1% BSA in 1× PBS). Shake on orbital shaker at room temperature for 1-2 hrs.

h.) Aspirate (or with beads and filter-plate use centrifuge or vacuum) and wash 3 times with 400 μl of wash buffer (e.g. 1% BSA in 1× PBS).

i.) Aspirate (or with beads and filter-plate use centrifuge or vacuum) plate.

j.) Add 50-100 μl elution buffer containing an acid solution with elemental spike, preferably an element that is soluble in the acid and close to the same atomic mass as the elements to be measured (e.g. 3% HCl, 1 ppb Pr). Shake on orbital shaker at room temperature for 5-10 minutes.

k.) Measure and quantitate elements of interest using atomic mass or optical spectrometer.

The kits may include two or more biologically active materials having distinguishable elemental tags for simultaneous determination of two or more analytes. In the case of kits for competition assays, the kits may include two or more competition analytes having distinguishable elemental tags and corresponding two or more capture molecules for the simultaneous determination of two or more analytes. Finally, the kits may also include a combination of components for the direct affinity assay, the sandwich affinity assay and the competitive affinity assay. For example, a tagged competition analyte is used to measure analyte A by a competition affinity assay and two differently tagged biologically active materials are used to measure analytes B and C by a direct affinity assay.

Example 20

Cytokine Immunoassay

Figure 8:
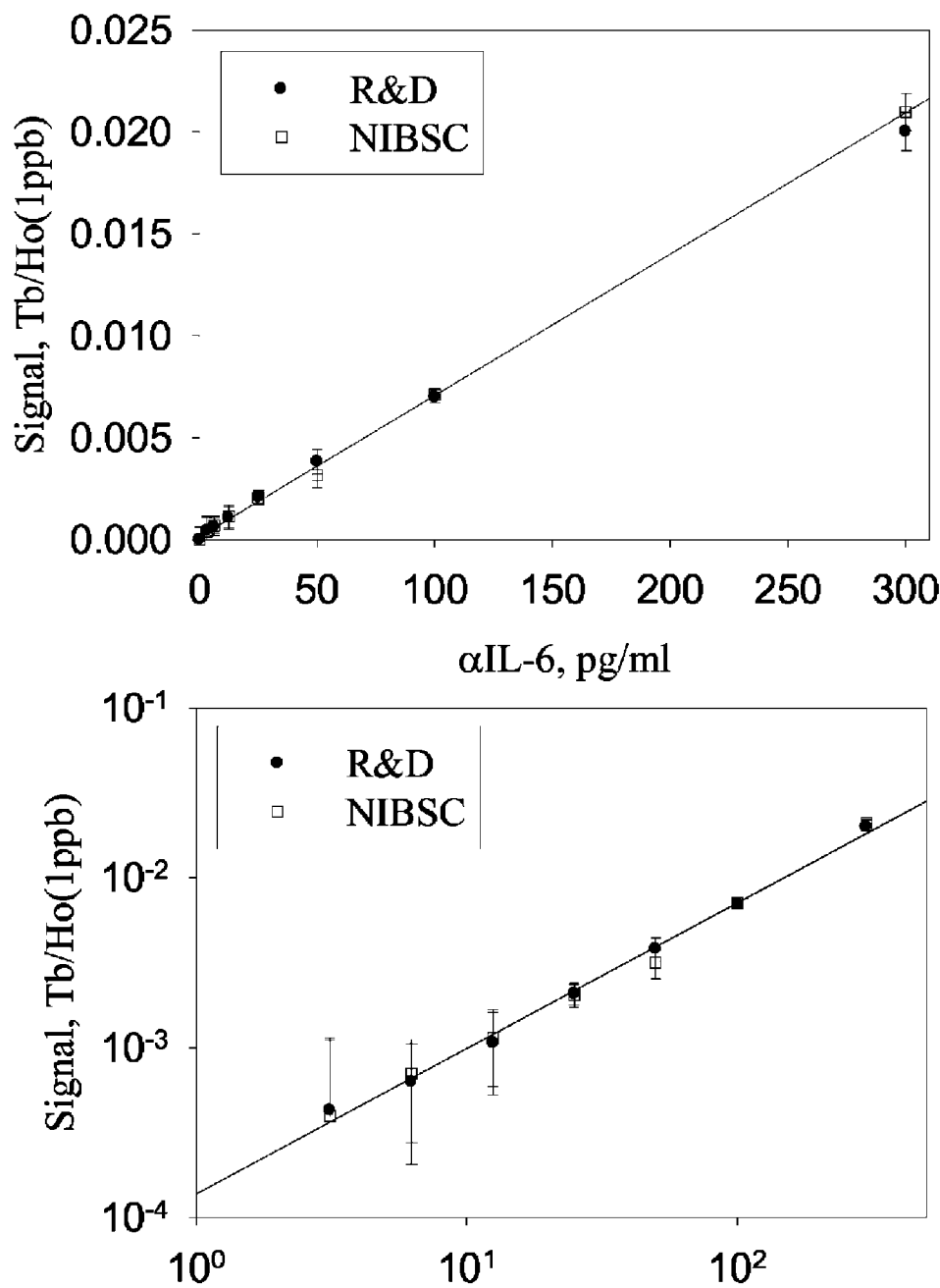
FIG. 8 shows two panels (in different scales on x-axis) of the same experiment in which an element-tagged sandwich assay was used to measure and quantitate two standards (provided by R&D systems and NIBSC) of cytokine Human Interleukin 6 (IL-6) using ICP-MS detection.

The following provides an example of the methods of the invention using element tags to determine the concentration of an analyte (eg. cytokine) of interest in a complex sample (FIGS. 6-11). Either NANOGOLD-Fab'™ or another element-labeled Fab' (or other biologically active material) that will bind specifically to the target analyte (or primary, secondary, or tertiary antibody) may be used. There are three types of immunoassays that may be used:

a) Direct immunoassay, which would involve trapping the protein(s) (Human IgG, FLAG-BAP, FIG. 6) or cytokine(s) of interest (Human Interferon gamma, IFN-g; Human Interleukin 5, IL-5, Human Interleukin 6, IL-6, and Human Interleukin 8, IL-8, FIG. 7) using a specified solid support such as microwell plates or microspheres (Maleic Anhydride microwell plates were used in experiment shown in FIG. 6 and Pall NT Acrowell Filter microwell plates were used in the experiment shown in FIG. 7), incubating with an excess of element-tagged (anti-Human IgG Fab'-nanoAu, FIG. 6; anti-IFN-.gamma.-Sm, anti-IL-5-Eu, anti-IL-6-Tb, and anti-IL-8-Dy, FIG. 7) or untagged primary antibody or other biologically active material (anti-BAP, FIG. 6) specific to the target analyte, washing off the un-reacted antibody, adding element-tagged secondary antibody (anti-mouse-Eu, FIG. 6), washing off un-reacted antibody and then subjecting the antibody-analyte complexes to atomic mass or optical spectrometry (eg. ICP-MS).

b) Sandwich immunoassay which would involve trapping the cytokine(s) of interest (IL-6 in FIG. 8; IL-6 and IL-8 in FIG. 9; IL-6, IL-8, IFN-.gamma. and TNF-.alpha. in FIG. 10; and IL-6 and TNF-.alpha. in FIG. 11) by incubating the sample containing the cytokine(s) of interest with a specified solid support such as the microwell plates (FIGS. 8-10) or microspheres (FIG. 11) that have been pretreated (bound) with an excess of primary antibody or biologically active material specific to the target analyte. The microwell plates or microspheres are washed to remove the un-reacted portion of the sample, and the cytokine is then exposed to element-tagged or untagged biologically active material (eg. primary antibody), washed to remove unreacted biologically active material, and if necessary incubated with element-tagged secondary antibody. The washed cytokine complexes are then subjected to atomic mass or optical spectrometry (eg. ICP-MS).

c) Competition immunoassay, which would involve trapping the target cytokine of interest (protein X) by incubating a specified solid support (eg. microwell plates or microspheres which may or may not be pretreated with an excess of primary antibody or biologically active material specific to the target analyte), adding the analyte-containing sample, washing off the unbound components, and then exposing the specified support with antibody-protein X complexes to a known amount of purified element-labeled protein X. The washed cytokine complexes are then subjected to atomic mass or optical spectrometry (eg. ICP-MS).

PBS buffer A is prepared as follows: 150 mM NaCl; 20 mM phosphate, pH 7.4; 1% BSA (bovine serum albumin). All eppendorf tubes, micro-titer plates, and filters, and slurry of microspheres to be used subsequently are treated with PBS buffer A for 1 hour at room temperature to block non-specific binding. This treatment will reduce the non-specific interactions that occur between the plastic used and the analyte and NANOGOLD-Fab'™. Alternatively low retention plastic products can be used (e.g. Axygen tubes). Following this a solution of the analyte (cytokine, peptide, protein, etc.) in a specified concentration range (eg. 1-100 ng/ml in FIG. 6; 0.1-10 ng/ml in FIG. 7; 3.12-300 pg/ml IL-6 in FIGS. 8, 9 and 10; 31.2-2000 pg/ml IL-8 in FIG. 9 and 10; 15.6-1000 pg/ml of IFN.gamma. and TNF-.alpha. in FIG. 10), 16-10,000 pg/ml of TNF-.alpha. and IL-6 in FIG. 11) in PBS buffer A or biological matrix (eg. EDTA plasma) is prepared. All dilutions are stored on ice. Subsequently, 100 ul of analyte or either PBS buffer A or other biological matrix such as EDTA-plasma (for negative controls) is pipetted into the individual wells of the micro-titer plate (or set of eppendorf tubes). If using NANOGOLD-Fab'™ to remove large unbound gold particles, the NANOGOLD-Fab'™ is pre-filtered through 300 KDa MICRCON™ (or CENTRICON™) centifugal filter devices. Filtered NANOGOLD-Fab'™ (and other element-tagged and untagged biologically active materials, eg. in FIG. 6, anti -Human IgG-Fab'-nanoAu, anti-BAP, anti-mouse-Eu; in FIG. 7, anti -IFN-.gamma.-Sm, anti-IL-5-Eu, anti-IL-6-Tb, and anti-IL-8-Dy; in FIG. 8, anti-IL-6-Tb; in FIG. 9, anti-IL-6-Tb, anti-IL-8-Dy; in FIG. 10, anti - IFN-.gamma.-Sm, anti-TNF-.alpha.-Eu, anti-IL-6-Tb, and anti-IL-8-Dy; and in FIG. 11, anti-TNF-.alpha.-Eu and anti-IL-6-Tb) required are diluted in PBS buffer A or other biological matrix such as EDTA-plasma are prepared as follows: a 1:50 dilution is produced by adding 60 µl of NANOGOLD-Fab'™ in 2940 µl PBS buffer A. A 1:500 dilution is then produced by adding 100 µ of 1:50 NANOGOLD-Fab'™ to 900 µl of PBS buffer A. In methods a) and b) depending on concentration range of analyte, 100 to 500 µl of 1:500 (or other suitable dilution) of NANOGOLD-Fab'™ (or other required element-tagged or untagged biologically active materials) is then added to the wells of the plate and then incubated for 1-2 hours at room temperature. In method c) an element-tagged analyte (cytokine) is added to each sample. In methods a-c) microwell plates are washed by pipetting fresh wash buffer in and out of wells 1-3 times. Microspheres in filter plates are washed through centrifugation of wash buffer (1-3 times). Microspheres in tubes are washed through centrifugation of wash buffer (1-3 times). Preferably all procedures are at 4 C. If an untagged biologically active material has been used in the proceeding step, the sample may be incubated with an element-tagged biologically active material (eg. secondary antibody) to bind the cytokine complex. The wash step will then need to be repeated. If an untagged biologically active material has been used in the proceeding step, the sample may be incubated with an element-tagged biologically active material (eg. tertiary antibody) to bind the cytokine complex. The wash step will then need to be repeated. Finally, a fixed volume of 10%HCl/1 ppbIr is added to each well. Ir and/or Ho provides an internal standard for ICP-MS quantitation and the acid solution is suitable for the elemental analysis.

Figure 6:
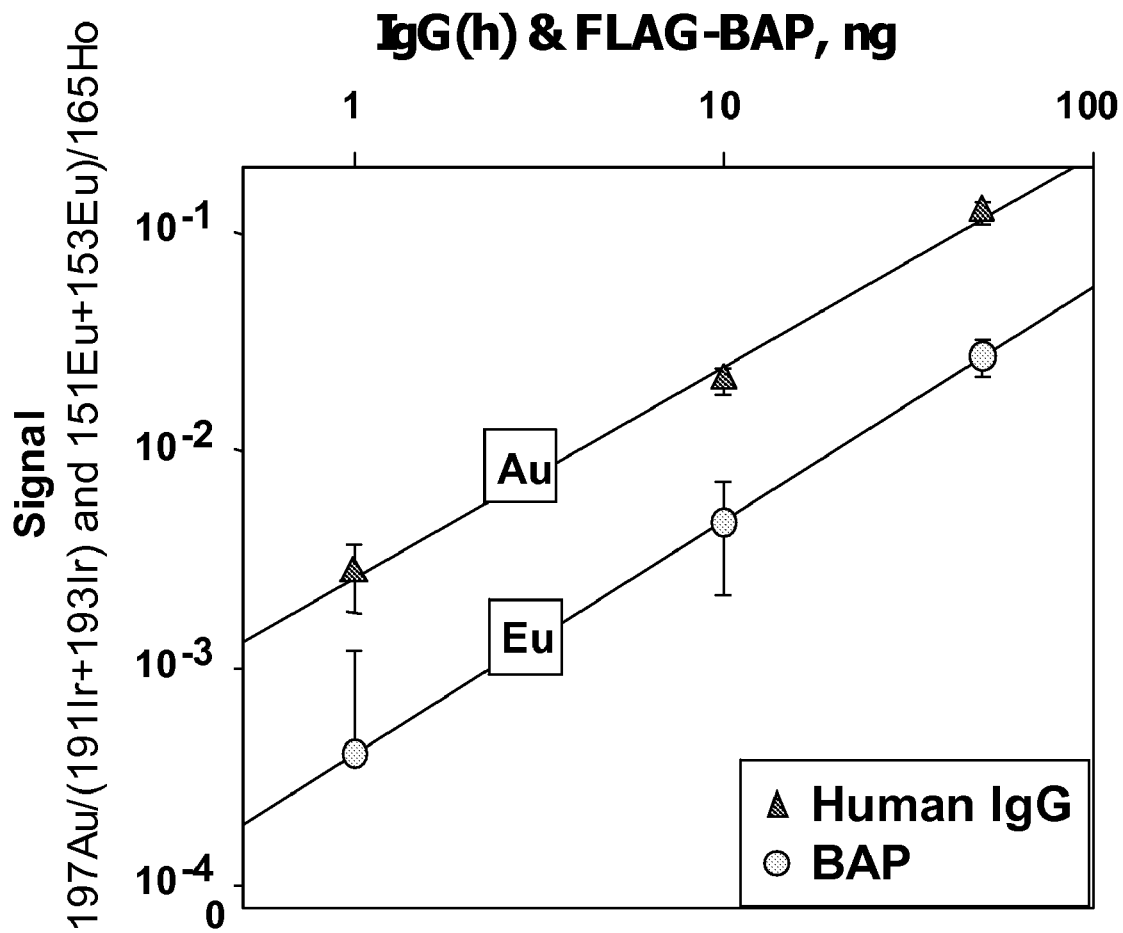
FIG. 6 is a graph showing the simultaneous detection and quantitation of two specific analytes (Human IgG and FLAG-Bacterial Alkaline Phosphatase, FLAG-BAP) using two different element tagged antibodies (anti-Human IgG-nanoAu and anti-mouse-Eu) in a single sample by ICP-MS.
Figure 7:
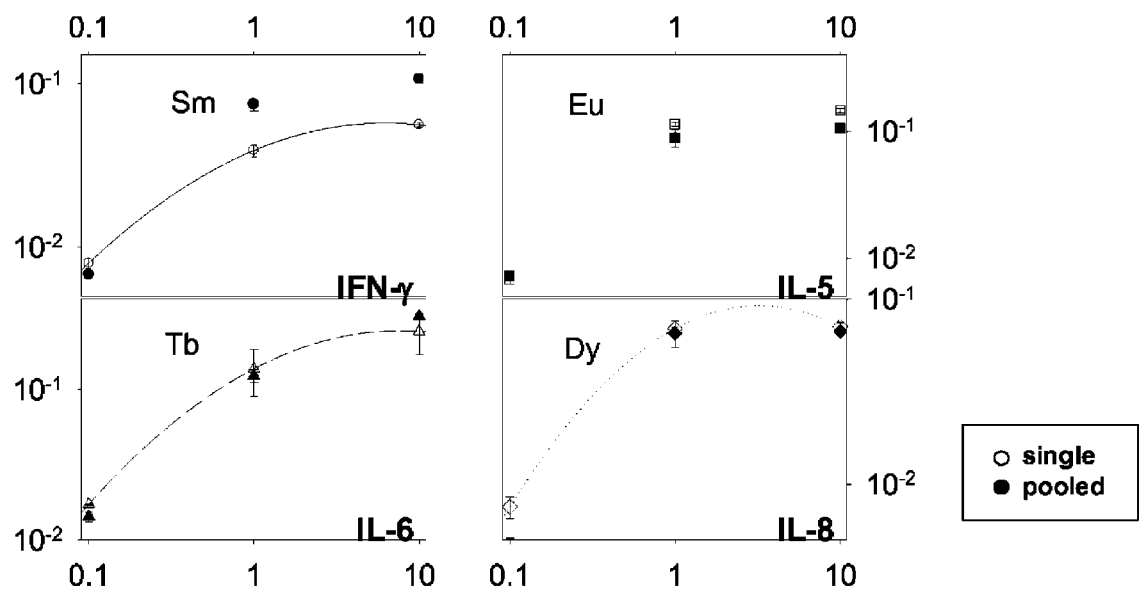
FIG. 7 shows the results of a direct immunoassay, using ICP-MS detection, of four human cytokines (Interferon-gamma, IFN-☐; Interleukin 5, IL-5; Interleukin 6, IL-6; and Interleukin 8, IL-8); simultaneously in pooled cytokine samples and singly in samples containing single cytokines.

Experimental results obtained according to method a) are given in FIGS. 6 and 7, using Human IgG and FLAG-BAP (FIG. 6) and IFN-.gamma., IL-5, Il-6, and IL-8 (FIG. 7) as the analytes of interest with anti-Human IgG F'ab-Au, anti-BAP and anti-mouse-Eu (FIG. 6), and anti-IFN-.gamma.-Sm, anti-IL-5-Eu, anti-IL-6-Tb, and anti-Il-8-Dy as the (un)tagged antibody (FIG. 7). Experimental results obtained according to method b) are given in FIGS. 8-11.

In FIG. 6, Maleic Anhydride microwell plates (Pierce) were used to anchor the proteins to the bottom of each of the 96 wells. Wells in triplicate contained concentrations of both Human IgG and FLAG-BAP in either 0, 1, 10 or 100 ng/ml in PBS buffer A. According to method a) Human IgG was bound with anti-Human IgG Fab'-nanoAu and FLAG-BAP was bound with anti-BAP and anti-mouse-Eu antibodies. Detection and quantitation was obtained using an ICP-MS.

In FIG. 7, Pall Acrowell filter plates were used to anchor the proteins to the bottom of each of the 96 wells. Wells in triplicate contained concentrations of both IFN-.gamma,. IL-5, IL-6, and IL-8 in either 0, 0.1, 1, or 10 ng/ml in PBS buffer A and according to method a) these human cytokines were bound with anti-IFN-.gamma.-Sm, anti-IL-5-Eu, anti-IL-6-Tb, and anti-IL-8-Dy antibodies respecitively. Detection and quantitation was obtained using an ICP-MS.

Figure 9:
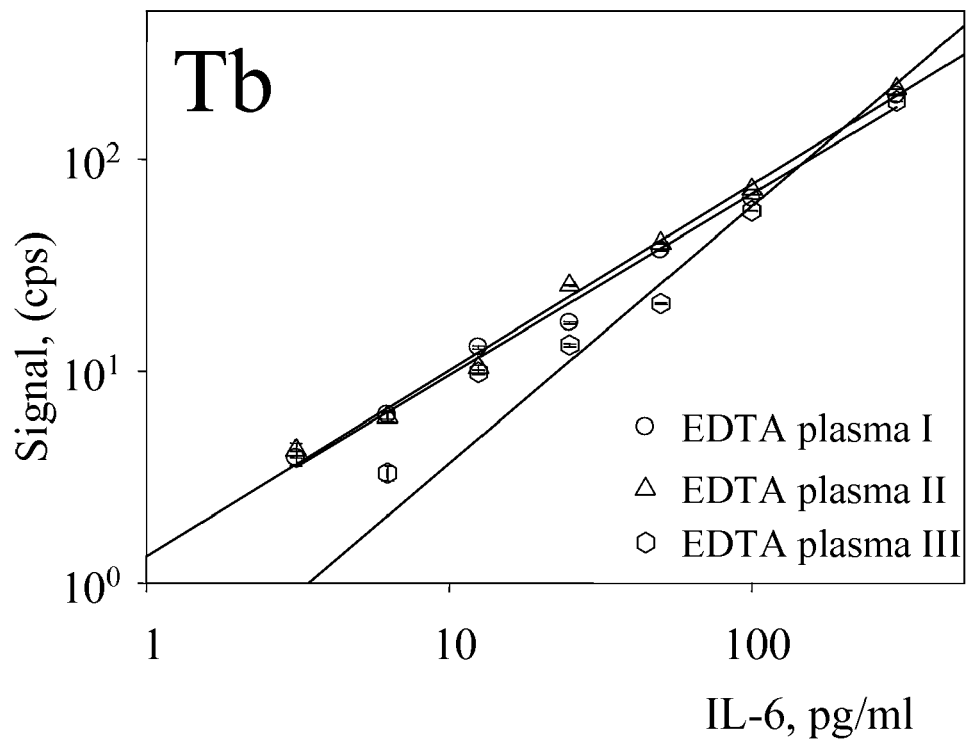
FIG. 9 shows the results from two experiments in which human cytokines (Interleukin 6, IL-6 and Interleukin 8, IL-8) were measured and quantitated in buffer (1% BSA, 1× PBS) and in complex biological mixtures (EDTA plasma from 3 patients: I, II and III) using element-tagged sandwich assays with ICP-MS detection.
Figure 9:
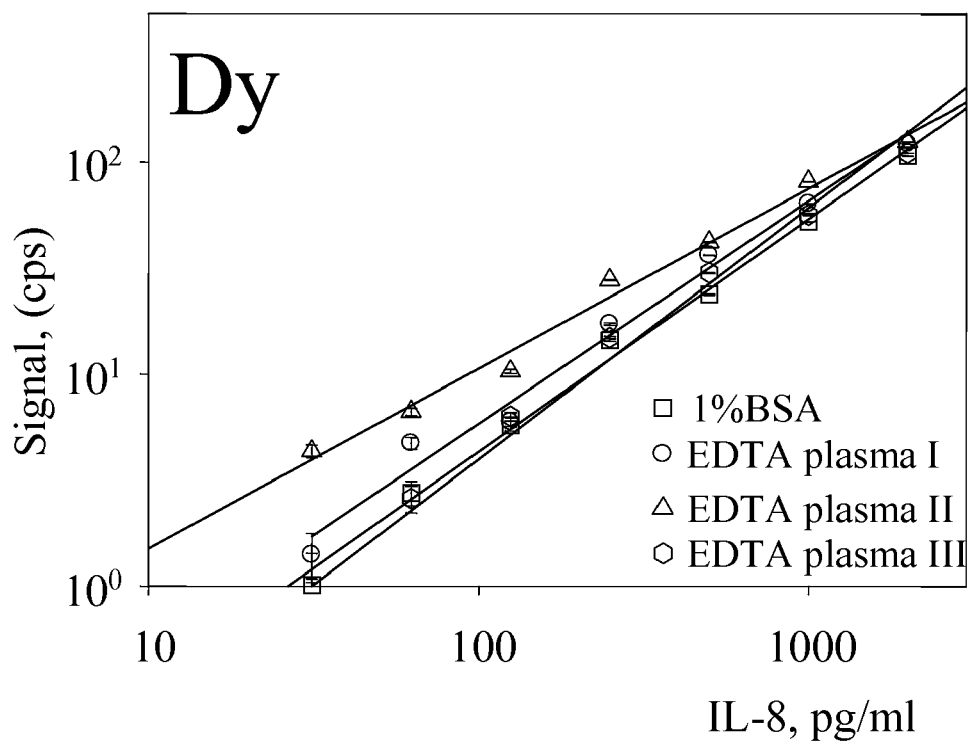
Figure 10:
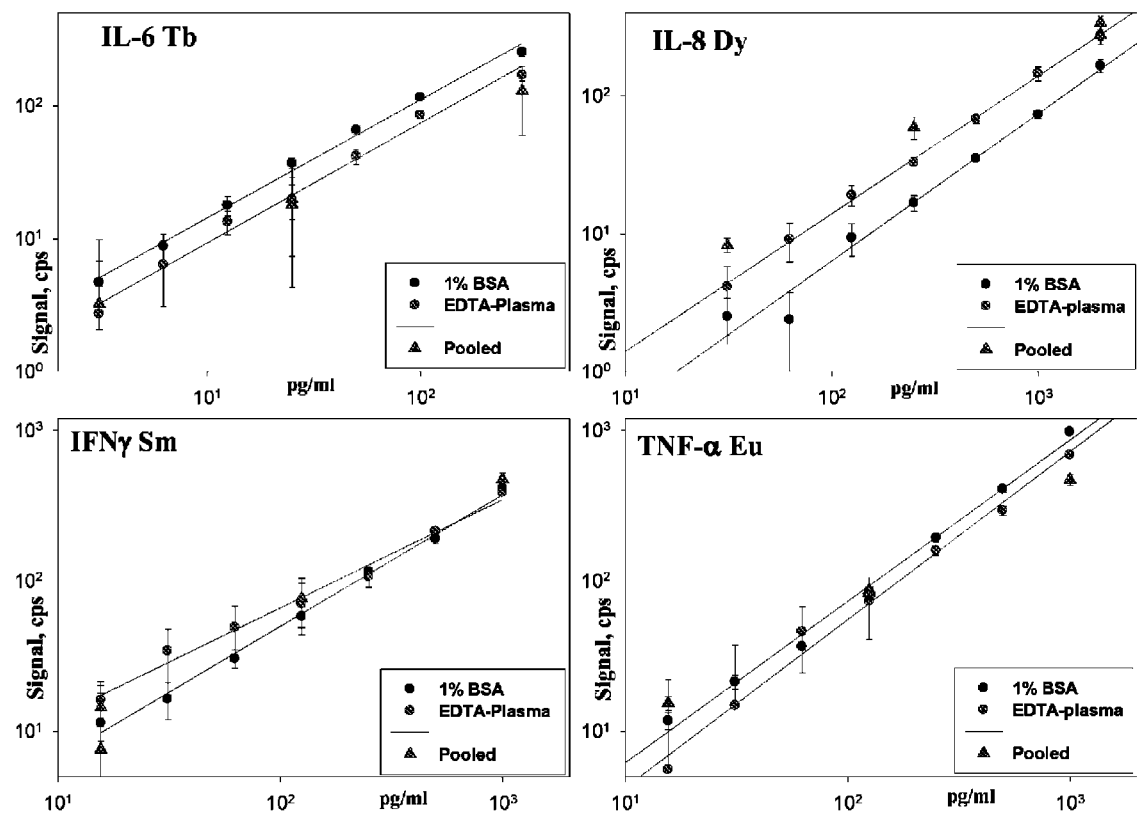
FIG. 10 shows the results from four experiments in which human cytokines (Interleukin 6, IL-6; Interleukin 8, IL-8; Interferon gamma, IFN☐, Tumor Necrosis Factor, TNF-☐) were measured and quantitated in buffer (1% BSA,1× PBS) and in a complex biological mixture (EDTA plasma) using element-tagged sandwich assays with ICP-MS detection. Cytokine concentrations were measured singly (red and black circles) or simultaneously in pooled samples (triangles).

In FIG. 8-10, Quantikine microwell plates (R&D systems) were used to anchor the proteins (cytokines) to the bottom of each of these 96 wells. Wells in triplicate contained concentrations of (as shown in graphs as well as 0 pg/ml for negative control) in PBS buffer A (or EDTA-plasma) and according to method b) these human cytokines were bound with specific element tagged antibodies (see FIGS. 8-10). Detection and quantitation was obtained using an ICP-MS.

Figure 11:
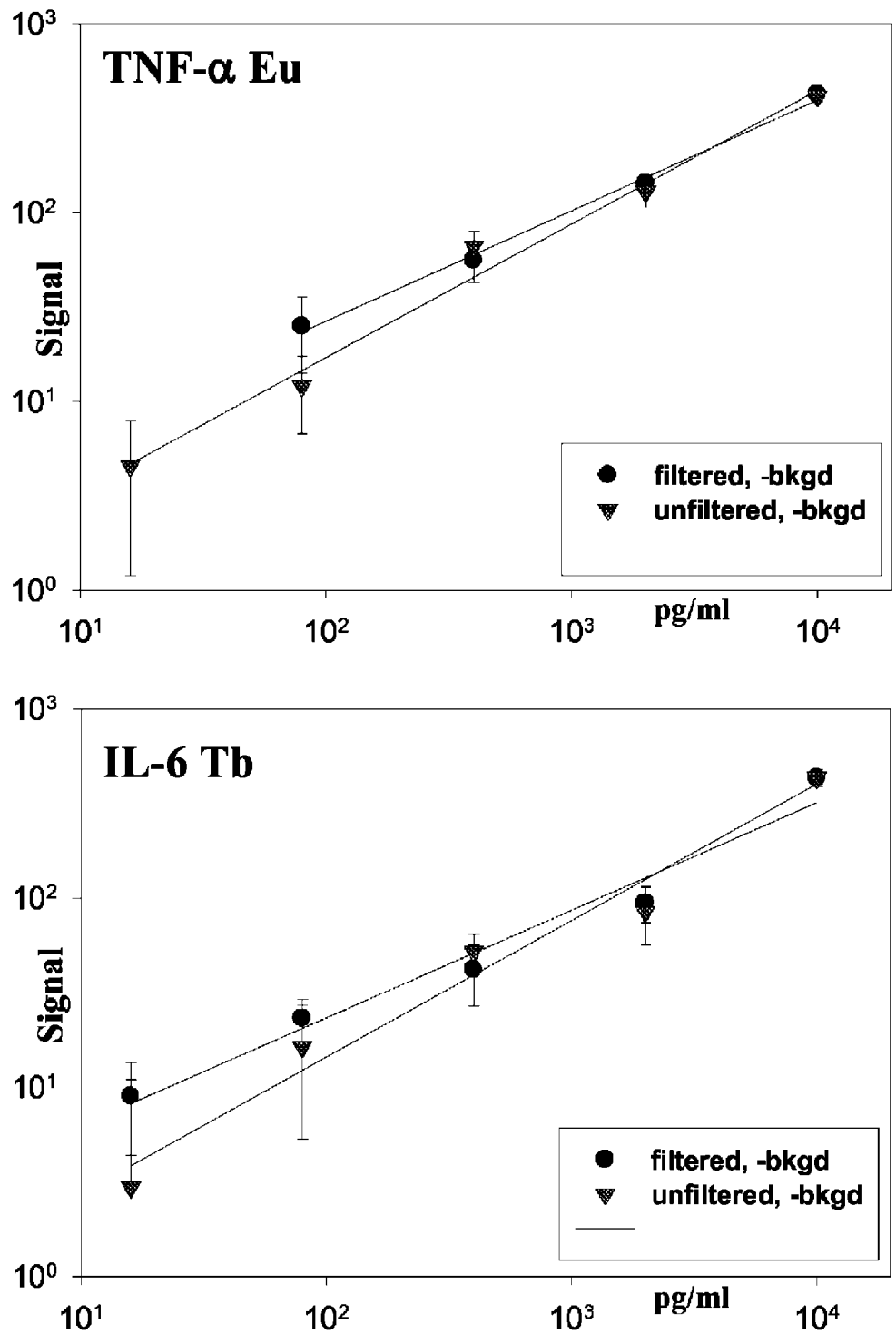
FIG. 11 shows the results of two experiments in which an element-tagged sandwich assay (using microspheres instead of a 96 well plate as a support for the assay) was used to simultaneously measure and quantitate 2 human cytokines (Tumor Necrosis Factor alpha, TNF-☐ and Interleukin 6, IL-6) using ICP-MS detection. In one experiment the filtrate of acidified microspheres was analyzed and in the second experiment unfiltered microspheres were analyzed directly by ICP-MS.

In FIG. 11, Fluorokine microspheres (R&D systems) were used to anchor the proteins (cytokines) and supplied filter plates were used to contain and perform each assay. Wells in triplicate contained concentrations of (as shown in graphs, as well as 0 pg/ml for negative control) in PBS buffer A and according to method b) these human cytokines were bound with specific element tagged antibodies (see FIG. 11). Detection and quantitation was obtained using an ICP-MS.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents, and parent applications are herein incorporated by reference in their entirety to the same extent as if each individual publication, patent or parent application was specifically and individually indicated to be incorporated by reference in its entirety.

REFERENCES

Baldwin, G. S., Hollande, F., Yang, Z., Karelina, Y., Peterson, A. Strang, R, Fourmy, D., Neumann, G., Shulkes, A. 2001 Biologically active recombinant human progastrin$_{6-80}$ contains a tightly bound calcium ion. J. Biol. Chem 276: 7791

Bandura D. R., Baranov V. I. and Tanner S. D. 2000. Effect of collisional damping and reactions in a dynamic reaction cell on the precision of the isotope ratio measurements. J. Anal. At. Spectrom., 15:921.

Baranov V. I., Tanner S. D. 1999 A dynamic reaction cell for inductively coupled plasma mass spectrometry (ICP-DRC-MS). Part I. The rf-field energy contribution in thermodynamics of ion-molecule reactions. J. Anal. At. Spectrom., 14:1133.

Barlett, P. A. et al, 1978 Synthesis of Water-Soluble Undecagold Cluster Compounds J. Am. Chem. Soc., 100: 5085

Bartel D. P. and Szostak J. W. 1993 Isolation of new ribozymes from a large pool of random sequences. Science: 261(1411-8).

Binet M. R. B., Ma, R., McLeod, C. and Poole, R. K. 2001 Detection of zinc/cadmium binding proteins in E. coli by gel electrophoresis-laser ablation-inductively coupled plasma-mass spectrometry. Society for Experimental Biology Annual Meeting April 2-6 C1.158 Canterbury, UK Bio-Rad PLATELIA™ BSE test (DAS-ELISA)

Blake, D. A., Blake II, R. C., Khosraviani, M., Pavlov, A. R. 1998 Immunoassays for metal ions. Analytica Chimica Acta 376: 13

Bordes, A. L., Schollborn, B., Limoges, B., and Degrand, C. 1999. Simultaneous detection of three drugs labelled by cationic metal complexes at a nafion-loaded carbon paste electrode. Talanta 48: 201.

Bosslet, K., Hermentin, P., Seemann, G. 1999 Monoclonal antibody against complexed and non-complexed complexing agents for removing heavy metals from aqueous solutions and for analysis. U.S. Pat. No. 5,907,034

Chen, X. Smith, L., Bradbury, E. 2000 Site-specific mass tagging with stable isotopes in proteins for accurate and efficient protein identification. Anal. Chem. 72: 1134-1143.

Cotton, F. A. and Wilkinson, G. 1972. Advanced Inorganic Chemistry, Interscience Publishers 528-530.

Darwish I. A. and Blake, D. A. 2001 One-step competitive immunoassay for cadmium ions: development and validation for environmental water samples. Analytical Chemistry 73: 1889

Ellington A. D. and Szostak J. W. 1990 In vitro selection of RNA molecules that bind specific ligands. Nature: 346 (6287), 818-822.

Ellington A. D. and Szostak J. W. 1992 Selection in vitro of single-stranded DNA molecules that fold into specific ligand-binding structures. Nature: 355(6363) 850-852.

Frackelton, Jr., Raymond, A., Eisen, H., Ross, 1985 A. Production and use of monoclonal antibodies to phosphotyrosine-containing proteins. U.S. Pat. No. 4,543,439.

Gillis, S 1983 Hybridoma antibody which inhibits interleukin 2 activity. U.S. Pat. No. 4,411,993.

Gold, L., Polisky, B., Uhlenbeck, O., and Yarus, M., 1995 Diversity of oligonucleotide functions. Annu. Rev. Biochem.: 64, 763-797.

Hainfeld, J., Leone, R., Furuya, F., Powell, R. 1996 Small organometallic probes. U.S. Pat. No. 5,521,289

Harlow and Lane (Eds) 1988 Antibodies: A Laboratroy Manual, Cold Spring Laboratroy Press Hinshaw, J., Toner, J., Reynolds, G., 1987 Fluorescent labels fro immunoassay. U.S. Pat. No. 4,637,988

Josel, H-P., Hoss, E., Ofenloch-Hahnle, B., Seidel, C., Upmeier, B., Wienhues, U-H. 1999 Metal complexes with a charged linker. U.S. Pat. No. 5,958,783

Kennet, McKearn, Bechtold (eds) 1980 Monoclonal antibodies hybridomas: A new dimension in biological analyses. Plenum Press.

Kohler, G and Milstein, C. 1975. Continuous cultures of fused cells secreting antibody of predefined specificity. Nature 256: 495.

Korth, C., Stierli, B., Streit, P., Moser, M., Schaller, O., Fischer, R., Schulz-Schaeffer, W., Kretzschmar, H., Raeber, A., Braun, U., Ehrensperger, F., Hornemann, S., Glockshuber, R., Riek, R., Billerter, M., Wuthrich, K., and Oesch, B. 1997. Prion (PrP$^{Sc}$)-specific epitope defined by a monoclonal antibody. Nature, 390(6655), 74-7.

Laffling, A. J., Baird, A., Birkett, C. R., and John, H. A. 2001. A monoclonal antibody that enables specific immunohistological detection of prion protein in bovine spongiform encephalopathy cases. Neurosci. Lett. 300(2), 99-102.

Leuvering, J. H. W. 1982. Metal Sol Particle Immunoassay. U.S. Pat. No. 4,313,734

Lorsch J. R. and Szostak J. W. 1994 In vitro selection of RNA aptamers specific for cyanocobalamin. Biochem.: 33(4), 973-982.

Martin de Llano, J., Andreu, E., and Knecht, E. 1996. Use of Inductively Coupled Plasma-Mass Spectrometry for the Quantitation of the Binding and Uptake of Colloidal Gold-Low Density Lipoprotein Conjugates by Cultured Cells. Analytical Biochm. 243: 210-217.

Martin de Llano, J., Andreu, E., Pastor, A., dela Guardia, M., Knecht, E. 2000. Electrothermal atomic absorption spectrometric diagnosis of familial hypercholesterolemia. Anal. Chem. 72: 2406-2413.

Nagaoka, M. and Maitani, T. 2000 Binding patterns of co-existing aluminium and iron to human serum transferrin studied by HPLC-high resolution ICP-MS. Analyst 135: 1962-1965.

Qiu, J., and Song, J. F. 1996 A rapid polarographic immunoassay based on the anodic current of metal labelling. Anal. Biochem. 240: 13-16.

Robertson D. L., Joyce G. F. 1990 Selection in vitro of an RNA enzyme that specifically cleaves single-stranded DNA. Nature: 344(6265), 467-468.

Segond von Banchet, G., and Heppelmann, B. 1995 Non-radioactive localization of substance P binding sites in rat brain and spinal cord using peptides labeled with 1.4 nm gold particles. J. Histochem. Cytochem. 43: 821-827.

Tanner S. D., Baranov V. I. 1999 A dynamic reaction cell for inductively coupled plasma mass spectrometry (ICP-DRC-MS). Part II. Reduction of interferences produced within the cell. JASMS, 101083.

Tanner S. D., Baranov V. I. and Vollkopf U. 2000a A dynamic reaction cell for inductively coupled plasma mass spectrometry (ICP-DRC-MS). Part III. Optimization and analytical performance; J. Anal. At. Spectrom., 15: 1261.

Tanner, S., Baranov, V. 2000b Bandpass reactive collision cell. U.S. Pat. No. 6,140,638.

Turek C., Gold L., 1990 Systematic evolution of ligands by exponential enrichment: RNA ligands to bacteriophage T4 DNA polymerase. Science: 249(4968), 505-510.

Wagenknecht, T., Berkowitz, J., Grassucci, R., Timerman. A. P., and Fleischer, S. 1994 Localization of calmodulin binding sites on the ryanodine receptor from skeletal muscle by electron microscopy. Biophys. J. 67: 2286-2295.

Wakabayashi, K., Sumi, Y., Ichikawa, Y., Sakato, Y., Mimuro, J., Aoki, N. 1990 Monoclonal antibody to human protein C. U.S. Pat. No. 4,902,614

Wang, C. 1984 Method of Tagged Immunoassay. U.S. Pat. No. 4,454,233.

Wenzel, T., and Baumeister, W. 1995 Conformational constraints in protein degradation by the 20S proteasome. Nature Structural Biol. 2: 199-204.

Wind, M., Edler, M., Jakubowski, N., Linscheid, M., Wesch, H., Lehmann, W. 2001 Analysis of protein phosphorylation by capillary liquid chromatography coupled to element mass spectrometry with $P^{31}$ detection and to electrospray mass spectrometry. Anal. Chem. 73: 29-35.

We claim:

1. A method for the detection and measurement of a positively charged transition element in a sample, where the measured transition element is a specific tag which is unnaturally bound on an aptamer, wherein the aptamer binds with an analyte or analyte complex, comprising:
   a) combining a tagged aptamer with the analyte or analyte complex, where the tagged aptamer binds with the analyte or analyte complex;
   b) separating the analyte or analyte complex which is bound to the tagged aptamer from unbound tagged aptamer; and
   c) detecting and measuring the positively charged transition element by one of an inductively coupled plasma mass spectrometer and an inductively coupled plasma optical emission spectrometer wherein said transition element is any element having an atomic number of 21-29, 39-47, 57-79 or 89.

2. A method for the detection and measurement of a positively charged transition element in a sample, where the measured transition element is a specific tag which is unnaturally bound on an aptamer wherein the aptamer binds with an analyte or analyte complex, comprising:
   a) combining the aptamer with the analyte or analyte complex;
   b) introducing the transition element to the combined aptamer and analyte or analyte complex, wherein the transition element binds with the aptamer; and
   c) detecting and measuring the positively charged transition element by one of an inductively coupled plasma mass spectrometer and an inductively coupled plasma optical emission spectrometer wherein said transition element is any element having an atomic number of 21-29, 39-47, 57-79 or 89.

3. A method for the detection and measurement of a positively charged transition element in a sample, where the measured transition element is a specific tag which is unnaturally bound on a competition analyte, comprising:
   a) combining a tagged competition analyte with at least one of an analyte and analyte complex, where the tagged competition analyte and at least one of the analyte and anlayte complex are in competition for a binding site;
   b) separating bound tagged competition analyte from the unbound tagged competition analyte; and
   c) detecting and measuring the positively charged transition element on the bound competition analyte by one of an inductively coupled plasma mass spectrometer and an inductively coupled plasma optical emission spectrometer wherein said transition element is any element having an atomic number of 21-29, 39-47, 57-79 or 89, wherein the detection and measurement of the transition element is related to the detection and measurement of at least one of the analyte and analyte complex.

4. The method of claim 3 wherein the binding site is located on a capture molecule.

5. A method for the detection and measurement of a positively charged transition element in a sample, where the measured transition element is a specific tag which is unnaturally bound on a biologically active affinity material, wherein the biologically active affinity material binds with an analyte or analyte complex, comprising:
   i) combining the tagged biologically active affinity material with the analyte or analyte complex, where the tagged biologically active affinity material binds with the analyte or analyte complex;
   ii) separating the analyte or analyte complex which is bound to the tagged biologically active affinity material from unbound tagged material; and
   iii) detecting and measuring the positively charged transition element by one of an inductively coupled plasma mass spectrometer and an inductively coupled plasma optical emission spectrometer wherein said transition element is any element having an atomic number of 21-29, 39-47, 57-79 or 89.

6. The method of claim 5 wherein the step ii) includes a step of electrophoresis of the analyte or analyte complex to separate the analyte or analyte complex which is bound to the tagged biologically active affinity material from the unbound tagged material.

7. The method of claim 5 wherein the analyte complex comprises a primary biologically active affinity material and an analyte, and wherein the tagged biologically active affinity material is a secondary biologically active affinity material tagged with the transition element.

8. The method of claim 5 wherein the tagged biologically active affinity material is a biologically active affinity material tagged with a nanoparticle having a metal core of 50-70 gold atoms.

9. The method of claim 5 wherein the step of detecting and measuring the positively charged transition element includes an inductively coupled plasma mass spectrometer.

10. The method of claim 5 wherein the transition element is an isotope.

11. The method of claim 5 wherein the transition element is selected from a group consisting of the noble metals, lanthanides, rare earth elements, gold, silver, platinum, rhodium, iridium and palladium.

12. The method of claim 5 wherein the transition element is gold, and wherein the gold has a diameter of 3 nm or less.

13. The method of claim 5 wherein the tagged biologically active affinity material comprises a covalent coupling of the transition element to the biologically active affinity material.

14. The method according to claim 5 wherein the biologically active affinity material is selected from a group consisting of an aptamer, antigen, hormone, growth factor, receptor, protein and nucleic acid.

15. The method of claim 5 wherein the tag is selected from the group consisting of a plurality of elements, a plurality of isotopes, a plurality of atoms of an isotope, a different number of atoms of each isotope, and combinations thereof, and wherein the step of detecting and measuring comprises detecting and measuring the transition element free of the analyte or analyte complex.

16. The method of claim 15 comprising an additional step of introducing two or more biologically active affinity materials or analytes having distinguishable elemental tags into a sample of interest for simultaneous determination, and wherein the step of detecting and measuring comprises detecting and measuring the transition element free of the analyte or analyte complex.

17. The method of claim 5 comprising an additional step of sample introduction to one of the atomic mass and optical spectrometer, wherein the sample introduction includes laser ablation.

18. The method of claim 5 which further comprises a step of running the analyte or analyte complex on an electrophoresis gel prior to the step of combining the tagged biologically active affinity material with the analyte or analyte complex, to isolate the analyte or analyte complex from the sample.

19. A method for the multiplexed detection and measurement of positively charged transition elements in a sample, wherein the measured transition elements are specific tags, each of which is unnaturally bound on a biologically active affinity material, and wherein the biologically active affinity material binds with an analyte or analyte complex, comprising:
　i) providing a plurality of biologically active affinity materials, wherein each biologically active affinity material of said plurality is tagged with at least one positively charged transition element in a manner that permits a given biologically active affinity material to be distinguished from other biologically active affinity materials of said plurality by an inductively coupled plasma spectrometer;
　ii) combining said materials with a plurality of analytes and/or analyte complexes, wherein said materials bind with the analyte or analyte complexes in a manner that permits a given analyte or analyte complex to be distinguished from other analytes or analyte complexes by an inductively coupled plasma spectrometer;
　iii) separating the analytes and/or analyte complexes that are bound to the tagged biologically active affinity materials from unbound tagged materials, and then
　iv) detecting and measuring, either simultaneously or sequentially, the positively charged transition elements with an inductively coupled plasma mass spectrometer or an inductively coupled plasma optical emission spectrometer, wherein said transition element is any element having an atomic number of 21-29, 39-47, 57-79 or 89.

20. The method according to claim 19, comprising detecting and measuring with an inductively coupled plasma mass spectrometer.

21. A method according to claim 19, wherein the positively charged transition elements comprise one or more isotopes of positively charged transition elements.

22. A method according to claim 19, wherein the step of detecting and measuring further comprises distinguishing one isotope of a transition element from one or more different isotopes of the same element or from one or more different elements.

23. The method of claim 19 comprising an additional step of introducing two or more biologically active affinity materials or analytes having distinguishable elemental tags into a sample of interest for simultaneous determination, and wherein the step of detecting and measuring comprises detecting and measuring the transition element free of the analyte or analyte complex.

24. The method of claim 19 wherein the biologically active affinity material is selected from the group consisting of an aptamer, antigen, hormone, growth factor, receptor, protein and nucleic acid.

25. The method of claim 5 wherein the analyte is a cytokine.

\* \* \* \* \*